US011419808B2

(12) United States Patent
Hilvert et al.

(10) Patent No.: US 11,419,808 B2
(45) Date of Patent: Aug. 23, 2022

(54) FIBROUS STRUCTURES CONTAINING CATIONIC SURFACTANTS AND SOLUBLE ACIDS

(71) Applicant: The Procter & Gamble Company, Cincinnati, OH (US)

(72) Inventors: Jennifer Elaine Hilvert, Cincinnati, OH (US); Mark William Hamersky, Hamilton, OH (US); Emily Lao Hickey, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 48 days.

(21) Appl. No.: 16/918,292

(22) Filed: Jul. 1, 2020

(65) Prior Publication Data

US 2021/0000733 A1    Jan. 7, 2021

Related U.S. Application Data

(60) Provisional application No. 62/870,312, filed on Jul. 3, 2019.

(51) Int. Cl.
*A61K 8/81* (2006.01)
*A61K 8/34* (2006.01)
*A61Q 5/12* (2006.01)

(52) U.S. Cl.
CPC ............ *A61K 8/8176* (2013.01); *A61K 8/342* (2013.01); *A61Q 5/12* (2013.01); *A61K 2800/30* (2013.01); *A61K 2800/5426* (2013.01)

(58) Field of Classification Search
None
See application file for complete search history.

(56) References Cited

U.S. PATENT DOCUMENTS

| | | |
|---|---|---|
| 2,356,168 A | 8/1944 | Mabley |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,613,185 A | 10/1952 | Marshall |
| 2,658,072 A | 11/1953 | Milton |
| 2,694,668 A | 11/1954 | Fricke |
| 2,809,971 A | 10/1957 | Bernstein et al. |
| 3,152,046 A | 10/1964 | Maria |
| 3,236,733 A | 2/1966 | Karsten et al. |
| 3,321,425 A | 5/1967 | Karl-ludwig et al. |
| 3,332,880 A | 7/1967 | Adriaan et al. |
| 3,426,440 A | 2/1969 | Shen et al. |
| 3,428,478 A | 2/1969 | Donaldson et al. |
| 3,463,308 A | 8/1969 | Deneke |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,929,678 A | 12/1975 | Laughlin |
| 3,967,921 A | 7/1976 | Haberli et al. |
| 4,020,156 A | 4/1977 | Murray et al. |
| 4,051,081 A | 9/1977 | Jabs et al. |
| 4,089,945 A | 5/1978 | Brinkman et al. |
| 4,149,551 A | 4/1979 | Benjamin et al. |
| 4,185,125 A | 1/1980 | Sakakibara et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| D266,829 S | 11/1982 | Yoshizawa et al. |
| 4,379,753 A | 4/1983 | Bolich, Jr. |
| 4,381,919 A | 5/1983 | Jacquet et al. |
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | De et al. |
| 4,536,361 A | 8/1985 | Torobin |
| 4,565,647 A | 1/1986 | Llenado |
| D286,450 S | 10/1986 | Tovey |
| 4,635,351 A | 1/1987 | Koch et al. |

(Continued)

FOREIGN PATENT DOCUMENTS

| | | |
|---|---|---|
| CA | 166297 | 5/2018 |
| CA | 169627 | 5/2018 |

(Continued)

OTHER PUBLICATIONS

All final and non-final office actions for U.S. Appl. No. 16/431,028.
All final and non-final office actions for U.S. Appl. No. 16/431,115.
All final and non-final office actions for U.S. Appl. No. 16/577,120.
All final and non-final office actions for U.S. Appl. No. 16/589,504.
All final and non-final office actions for U.S. Appl. No. 16/912,876.
All final and non-final office actions for U.S. Appl. No. 29/672,822.
All final and non-final office actions for U.S. Appl. No. 29/676,338.
All final and non-final office actions for U.S. Appl. No. 29/707,807.
All final and non-final office actions for U.S. Appl. No. 29/707,809.
All final and non-final office actions for U.S. Appl. No. 29/728,687.
All final and non-final office actions for U.S. Appl. No. 29/728,688.
All final and non-final Office Actions, U.S. Appl. No. 15/979,961.

(Continued)

*Primary Examiner* — Nannette Holloman
(74) *Attorney, Agent, or Firm* — Alexandra S. Anoff

(57) ABSTRACT

A fibrous structure with a plurality of fibrous elements. The fibrous elements contain a polymeric structurant; a fatty material with a melting point above 25° C.; a cationic surfactant, which can be selected from the group consisting of a mono-long alkyl amine, a tertiary amine, and combinations thereof; and an oil soluble acid. The oil soluble acid can be selected from the group consisting of salicylic acid, lactic acid, acetic acid, malic acid, succinic acid, sorbic acid, 2,4-dihydroxybenzoic acid, maleic acid, and combinations thereof.

17 Claims, 5 Drawing Sheets

(56) References Cited

U.S. PATENT DOCUMENTS

| | | |
|---|---|---|
| 4,663,158 A | 5/1987 | Wolfram et al. |
| 4,710,374 A | 12/1987 | Grollier et al. |
| 4,727,410 A | 2/1988 | Higgins, III |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,102,129 A | 4/1992 | Roberts |
| 5,104,646 A | 4/1992 | Bolich, Jr. |
| 5,106,609 A | 4/1992 | Bolich, Jr. |
| 5,166,276 A | 11/1992 | Hayama et al. |
| D334,420 S | 3/1993 | Copeland et al. |
| 5,220,033 A | 6/1993 | Kamei et al. |
| 5,261,426 A | 11/1993 | Kellett et al. |
| 5,280,079 A | 1/1994 | Allen et al. |
| RE34,584 E | 4/1994 | Grote et al. |
| D351,345 S | 10/1994 | Geho |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee |
| 5,429,628 A | 7/1995 | Trinh et al. |
| 5,455,114 A | 10/1995 | Ohmory |
| 5,457,895 A | 10/1995 | Thompson et al. |
| 5,458,433 A | 10/1995 | Stastny |
| 5,476,597 A | 12/1995 | Sakata et al. |
| 5,501,238 A | 3/1996 | Borstel et al. |
| 5,533,638 A | 7/1996 | Reiker |
| 5,580,481 A | 12/1996 | Sakata et al. |
| 5,582,786 A | 12/1996 | Brunskill et al. |
| D378,180 S | 2/1997 | Hayes |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,750,122 A | 5/1998 | Evans |
| 5,780,047 A | 7/1998 | Kamiya et al. |
| D398,847 S | 9/1998 | Wyslotsky |
| D399,260 S | 10/1998 | Thimote |
| D407,640 S | 4/1999 | Crapser et al. |
| D408,223 S | 4/1999 | Henry |
| 5,911,224 A | 6/1999 | Berger |
| 5,925,603 A | 7/1999 | D, Angelo |
| 5,955,419 A | 9/1999 | Barket, Jr. et al. |
| D416,103 S | 11/1999 | Hashmi |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D441,869 S | 5/2001 | Bloor et al. |
| D442,353 S | 5/2001 | Macias |
| D442,739 S | 5/2001 | Friesenhahn |
| D443,389 S | 6/2001 | Friesenhahn |
| D448,802 S | 10/2001 | Lariviere, Jr. et al. |
| D449,881 S | 10/2001 | Mock, Sr. |
| D450,378 S | 11/2001 | Minakuchi et al. |
| 6,365,142 B1 | 4/2002 | Tamura |
| D462,900 S | 9/2002 | Yamada et al. |
| 6,458,754 B1 | 10/2002 | Velazquez et al. |
| D465,303 S | 11/2002 | Friesenhahn |
| 6,503,521 B1 | 1/2003 | Atis et al. |
| 6,525,034 B2 | 2/2003 | Dalrymple et al. |
| D479,561 S | 9/2003 | Meyer |
| D484,749 S | 1/2004 | Garraway |
| D489,162 S | 5/2004 | Dings-plooij |
| 6,790,814 B1 | 9/2004 | Marin |
| 6,800,295 B2 | 10/2004 | Fox |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| D509,935 S | 9/2005 | Burt |
| 6,943,200 B1 | 9/2005 | Corrand et al. |
| D515,915 S | 2/2006 | Karim |
| 7,015,181 B2 | 3/2006 | Lambino |
| 7,208,460 B2 | 4/2007 | Shefer et al. |
| D549,051 S | 8/2007 | Nordwall |
| 7,285,520 B2 | 10/2007 | Krzysik |
| 7,387,787 B2 | 6/2008 | Fox |
| D576,753 S | 9/2008 | Mukai |
| D577,332 S | 9/2008 | Moore |
| D578,881 S | 10/2008 | Friedland |
| D588,332 S | 3/2009 | Phelan |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| D644,541 S | 9/2011 | Schrader et al. |
| D651,096 S | 12/2011 | Nakagiri |
| D655,154 S | 3/2012 | Amos |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,546,640 B2 | 10/2013 | Popovsky et al. |
| D694,621 S | 12/2013 | McCarthy |
| 8,723,333 B2 | 5/2014 | Park et al. |
| 8,765,170 B2 | 7/2014 | Glenn, Jr. |
| D712,159 S | 9/2014 | Clerici et al. |
| D712,822 S | 9/2014 | Brusaw et al. |
| 9,062,186 B2 | 6/2015 | Longdon et al. |
| D739,227 S | 9/2015 | Mitchell et al. |
| D740,928 S | 10/2015 | Bruining et al. |
| 9,198,838 B2 | 12/2015 | Glenn, Jr. |
| D748,240 S | 1/2016 | Goode |
| D769,522 S | 10/2016 | Venet |
| D771,788 S | 11/2016 | Duckwitz |
| D774,086 S | 12/2016 | Montes et al. |
| D775,198 S | 12/2016 | Montes |
| 9,539,444 B2 | 1/2017 | Kinoshita et al. |
| D778,026 S | 2/2017 | Roetheli |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| D811,922 S | 3/2018 | Lefave |
| D811,935 S | 3/2018 | Hughes |
| D819,836 S | 6/2018 | Noël |
| D848,102 S | 5/2019 | Carlson et al. |
| D850,041 S | 5/2019 | Endie |
| 10,294,586 B2 | 5/2019 | Sivik et al. |
| D851,344 S | 6/2019 | Carlson et al. |
| D857,156 S | 8/2019 | Hani |
| D857,242 S | 8/2019 | Darrow et al. |

(56) References Cited

U.S. PATENT DOCUMENTS

| | | |
|---|---|---|
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton et al. |
| D866,105 S | 11/2019 | Carlson et al. |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| D901,115 S | 11/2020 | Carlson et al. |
| D903,152 S | 11/2020 | Chao |
| D906,802 S | 1/2021 | Chi |
| D910,434 S | 2/2021 | Tan et al. |
| D910,457 S | 2/2021 | Lee |
| D921,166 S | 6/2021 | Meyers |
| D933,095 S | 10/2021 | Heiner et al. |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada et al. |
| 2002/0187181 A1 | 12/2002 | Godbey et al. |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan |
| 2003/0099691 A1 | 5/2003 | Lydzinski et al. |
| 2003/0099692 A1 | 5/2003 | Lydzinski et al. |
| 2003/0141662 A1 | 7/2003 | Kost et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0209166 A1 | 11/2003 | Vanmaele et al. |
| 2003/0215522 A1 | 11/2003 | Johnson et al. |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott |
| 2004/0053808 A1 | 3/2004 | Raehse et al. |
| 2004/0059055 A1 | 3/2004 | Inada |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey et al. |
| 2004/0126585 A1 | 7/2004 | Kerins et al. |
| 2004/0175404 A1 | 9/2004 | Shefer |
| 2004/0180597 A1 | 9/2004 | Kamada |
| 2004/0202632 A1 | 10/2004 | Gott et al. |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2005/0069575 A1 | 3/2005 | Fox |
| 2005/0136780 A1 | 6/2005 | Clark et al. |
| 2005/0137272 A1 | 6/2005 | Gaserod |
| 2005/0159730 A1 | 7/2005 | Kathrani et al. |
| 2005/0202992 A1 | 9/2005 | Grandio et al. |
| 2005/0220745 A1 | 10/2005 | Lu |
| 2005/0232954 A1 | 10/2005 | Yoshinari et al. |
| 2005/0272836 A1 | 12/2005 | Yaginuma et al. |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0128592 A1 | 6/2006 | Ross |
| 2006/0159730 A1 | 7/2006 | Simon |
| 2006/0228319 A1 | 10/2006 | Vona, Jr. et al. |
| 2006/0274263 A1 | 12/2006 | Yacktman et al. |
| 2007/0028939 A1 | 2/2007 | Mareri et al. |
| 2007/0099813 A1 | 5/2007 | Luizzi |
| 2007/0110792 A9 | 5/2007 | Simon |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2008/0019935 A1 | 1/2008 | Khan |
| 2008/0035174 A1 | 2/2008 | Aubrun-sonneville |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0152894 A1 | 6/2008 | Beihoffer et al. |
| 2008/0153730 A1 | 6/2008 | Tsaur |
| 2008/0215023 A1 | 9/2008 | Scavone et al. |
| 2008/0276178 A1 | 11/2008 | Fadell et al. |
| 2008/0292669 A1 | 11/2008 | Deng et al. |
| 2008/0293839 A1 | 11/2008 | Stobby |
| 2009/0197787 A1 | 8/2009 | Venet et al. |
| 2009/0232873 A1 | 9/2009 | Glenn, Jr. et al. |
| 2009/0263342 A1 | 10/2009 | Glenn, Jr. |
| 2010/0018641 A1 | 1/2010 | Branham |
| 2010/0150976 A1 | 6/2010 | Schnitzler |
| 2010/0167971 A1 | 7/2010 | Glenn, Jr. et al. |
| 2010/0173817 A1 | 7/2010 | Glenn, Jr. et al. |
| 2010/0286011 A1 | 11/2010 | Glenn, Jr. et al. |
| 2010/0291165 A1 | 11/2010 | Glenn, Jr. et al. |
| 2011/0023240 A1 | 2/2011 | Fossum |
| 2011/0027328 A1 | 2/2011 | Baig et al. |
| 2011/0028374 A1 | 2/2011 | Fossum et al. |
| 2011/0033509 A1 | 2/2011 | Simon |
| 2011/0165110 A1 | 7/2011 | Kinoshita et al. |
| 2011/0182956 A1 | 7/2011 | Glenn, Jr. et al. |
| 2011/0189247 A1 | 8/2011 | Glenn, Jr. |
| 2011/0195098 A1 | 8/2011 | Glenn, Jr. |
| 2011/0250256 A1 | 10/2011 | Hyun-oh et al. |
| 2011/0287687 A1 | 11/2011 | Kramer et al. |
| 2012/0021026 A1 | 1/2012 | Glenn, Jr. |
| 2012/0052036 A1 | 3/2012 | Glenn, Jr. |
| 2012/0052037 A1 | 3/2012 | Sivik et al. |
| 2012/0107534 A1 | 5/2012 | Wnuk et al. |
| 2012/0237576 A1 | 9/2012 | Gordon |
| 2012/0270029 A1 | 10/2012 | Glenn, Jr. et al. |
| 2012/0294823 A1 | 11/2012 | Aramwit |
| 2012/0321580 A1 | 12/2012 | Glenn, Jr. |
| 2013/0236520 A1 | 9/2013 | Popovsky et al. |
| 2013/0303419 A1 | 11/2013 | Glenn, Jr. et al. |
| 2014/0271744 A1 | 9/2014 | Glenn, Jr. et al. |
| 2014/0329428 A1 | 11/2014 | Glenn, Jr. |
| 2015/0102307 A1 | 4/2015 | Tajima et al. |
| 2015/0297494 A1 | 10/2015 | Mao |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0101026 A1 | 4/2016 | Pratt |
| 2016/0101204 A1 | 4/2016 | Lynch et al. |
| 2016/0143827 A1 | 5/2016 | Castan Barberan et al. |
| 2016/0250109 A1 | 9/2016 | Dreher et al. |
| 2016/0367104 A1 | 12/2016 | Dreher et al. |
| 2017/0121641 A1 | 5/2017 | Smith |
| 2017/0335080 A1 | 11/2017 | Mao et al. |
| 2018/0140469 A1 | 5/2018 | Kane et al. |
| 2018/0311135 A1 | 11/2018 | Chang et al. |
| 2018/0333339 A1 | 11/2018 | Hamersky |
| 2018/0334644 A1 | 11/2018 | Hamersky et al. |
| 2019/0015875 A1 | 1/2019 | Gardner, Jr. et al. |
| 2019/0282457 A1 | 9/2019 | Pratt |
| 2019/0282461 A1 | 9/2019 | Glassmeyer |
| 2019/0350819 A1 | 11/2019 | Hamersky et al. |
| 2020/0093710 A1 | 3/2020 | Hamersky |
| 2020/0214946 A1 | 7/2020 | Chan et al. |
| 2020/0308360 A1 | 10/2020 | Mao et al. |

(56) References Cited

U.S. PATENT DOCUMENTS

| | | |
|---|---|---|
| 2020/0405587 A1 | 12/2020 | Song |
| 2021/0094744 A1 | 4/2021 | Benson et al. |
| 2021/0107263 A1 | 4/2021 | Bartolucci et al. |
| 2021/0147763 A1 | 5/2021 | Tan et al. |
| 2021/0401677 A1 | 12/2021 | Song |

FOREIGN PATENT DOCUMENTS

| | | |
|---|---|---|
| CN | 1138091 | 12/1996 |
| CN | 1219388 | 6/1999 |
| CN | 1268558 | 10/2000 |
| CN | 1357613 A | 7/2002 |
| CN | 1473194 A | 2/2004 |
| CN | 1530431 A | 9/2004 |
| CN | 1583991 A | 2/2005 |
| CN | 3648760 | 5/2007 |
| CN | 102006852 A | 4/2011 |
| CN | 301666535 | 9/2011 |
| CN | 102647973 A | 8/2012 |
| CN | 103282015 A | 9/2013 |
| CN | 103735428 A | 4/2014 |
| CN | 104040061 A | 9/2014 |
| CN | 304115833 | 4/2017 |
| CN | 106726634 A | 5/2017 |
| CN | 106728634 A | 5/2017 |
| CN | 304537587 | 3/2018 |
| CN | 109589279 B | 3/2020 |
| DE | 19607851 A1 | 9/1997 |
| DE | 10331767 A1 | 2/2005 |
| DE | 100932 | 4/2018 |
| DE | 100938 | 4/2018 |
| DE | 101063 | 5/2018 |
| DE | 101100 | 5/2018 |
| DE | 101101 | 5/2018 |
| EP | 609808 A1 | 8/1994 |
| EP | 0858828 A1 | 8/1998 |
| EP | 1217987 B1 | 12/2004 |
| EP | 1160311 B1 | 3/2006 |
| EP | 1958532 A2 | 8/2008 |
| EP | 2085434 A1 | 8/2009 |
| EP | 1317916 B1 | 10/2010 |
| FR | 2871685 A1 | 12/2005 |
| FR | 2886845 A1 | 12/2006 |
| GB | 2235204 A | 2/1991 |
| GB | 2355008 A | 4/2001 |
| JP | 58021608 | 2/1983 |
| JP | S58216109 A | 12/1983 |
| JP | S6272609 A | 4/1987 |
| JP | S6272610 A | 4/1987 |
| JP | S6281432 A | 4/1987 |
| JP | H01172319 A | 12/1987 |
| JP | H01313418 A | 12/1989 |
| JP | H0275650 A | 3/1990 |
| JP | H05344873 A | 12/1993 |
| JP | H0617083 A | 1/1994 |
| JP | 0753349 | 2/1995 |
| JP | H0789852 A | 4/1995 |
| JP | H08325133 A | 12/1996 |
| JP | H09216909 A | 8/1997 |
| JP | H10251371 A | 9/1998 |
| JP | 2000053998 A | 2/2000 |
| JP | 2003073700 A | 3/2003 |
| JP | 2003082397 A | 3/2003 |
| JP | 2004256799 A | 9/2004 |
| JP | 2004345983 A | 12/2004 |
| JP | 2005171063 A | 6/2005 |
| JP | 2007091954 A | 4/2007 |
| JP | 2007197540 A | 8/2007 |
| KR | 20020003442 A | 1/2002 |
| WO | 8301943 A1 | 6/1983 |
| WO | 9514495 A1 | 6/1995 |
| WO | 0119948 A1 | 3/2001 |
| WO | 0125393 A1 | 4/2001 |
| WO | 200125322 A1 | 4/2001 |
| WO | 2001024770 A1 | 4/2001 |
| WO | 2001054667 A1 | 8/2001 |
| WO | 0238722 A2 | 5/2002 |
| WO | 2004032859 A1 | 4/2004 |
| WO | 2004041991 A1 | 5/2004 |
| WO | 2005003423 A1 | 1/2005 |
| WO | 2005070374 A1 | 8/2005 |
| WO | 2005075547 A1 | 8/2005 |
| WO | 2007033598 A1 | 3/2007 |
| WO | 2007093558 A1 | 8/2007 |
| WO | 2009019571 A1 | 2/2009 |
| WO | 2009095891 A1 | 8/2009 |
| WO | 2010077627 A2 | 7/2010 |
| WO | 2010085569 A1 | 7/2010 |
| WO | 2012120199 A1 | 9/2012 |
| WO | 2019001940 A1 | 1/2019 |

OTHER PUBLICATIONS

All final and non-final Office Actions, U.S. Appl. No. 15/981,096.
PCT International Search Report and Written Opinion for PCT/US2018/015363 dated Jun. 4, 2018.
PCT International Search Report and Written Opinion for PCT/US2018/015364 dated Oct. 1, 2018.
PCT International Search Report and Written Opinion for PCT/US2018/030762 dated Aug. 7, 2018.
Definition of Derivative by Merriam Webster Online Dictionary, Year, 2021.
Wermuth et al. Drug Discovery, "Drug Discovery Today, 2006", vol. 11 7/8, 348-354, Year 2006.
Adhesives Research (Pennsylvania, http://12.4.33.51/news/apresmed.htm).
All final and non-final office actions for U.S. Appl. No. 14/690,593.
All final and non-final office actions for U.S. Appl. No. 15/665,886.
All final and non-final office actions for U.S. Appl. No. 16/901,548.
All Office Actions, U.S. Appl. No. 16/953,975.
All Office Actions, U.S. Appl. No. 17/070,205.
All Office Actions, U.S. Appl. No. 29/766,885.
Amerilab Technologies, Inc. (Minnesota, http://www.amerilabtech.comm/).
Anonymous "P8136 Poly(vinyl alcohol)" Internet article, [Online] XP002538935 retrieved from the Internet: URL:hllp/20NWW.sigmaaldrich.com/catalog/ProductDetail.do?D7=0%N25-SEARCH_ CONCAT PNOIBRAND KEY%N4=P8136%7SCIAL%N25=0%QS=ON%F=SPEC retrieved on Jul. 28, 2009.
Briscoe et al. "The effects of hydrogen bonding upon the viscosity of aqueous poly( vinyl alcohol) solutions," from Polymer, 41 (2000), pp. 3851-3860.
Cardinal Health (Dublin, Ohio, http://spd.cardinal.com/).
Cima Labs, Inc. (Minnesota, http://www.cimalabs.com/).
Design of "Detergent tablets" (Design Registration No. 000634142-0003), (No. of Publicly known information: HH18274488), Registered Community Designs Bulletin, published by EUIPO on Jan. 9, 2007.
Design of "Detergent tablets" (Design Registration No. 000634142-0004), (No. of Publicly known information: HH18274489), Registered Community Designs Bulletin, published by EUIPO on Jan. 9, 2007.
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612).
Dissolving Soap Strips (Ranir LLC, Michigan, www.ranir.com).
Encyclopedia of Polymer Science and Engineering, vol. 15, 2nd ed., pp. 204 308 Silicones, 1989.
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hexagon 4 ward soap mold, Soap, Cosmetics, NEW Silicon mold, Published on Sep. 29, 2016, Retrieved from Internet:http://candle-box.com/product/%EC%9C%A1%EA%B0%81-4%EA%B5%AC-%EB%B9%84%EB%88%84%EB%AA%B0%EB%93%9C/2206/?page_4=3#none.

(56) References Cited

OTHER PUBLICATIONS

Hildebrand, T., et al. "Quantification of bone microarchitecture with the structure mode index", Computer Methods in Biomechanics and Biomedical Engineering, vol. 1, Jan. 14, 1997, pp. 15-23.
How Gemz work?, Gemz Hair Care, published on Oct. 1, 2018, retrieved on Apr. 27, 2021, retrieved from the Internet URL: https://www.youtube.com/watch?v=ts1waYk43g4.
https://www.craftcuts.com/hexagon-craft-shape.htmlHexagon wood cutouts, www.craftcuts.com, 1 page, reviewed as early as May 2018 (Year: 2018).
International Search Report and Written Opinion; Application No. US2020/070216 dated Oct. 9, 2020; 12 pages.
Japanese Paper Soap (http://www.wishingfish.com/papersoap.html).
Kuraray: "Mowiol—Technical data sheet", Jun. 1, 2010 (Jun. 1, 2010),pp. 1-4, XP055119891, Retrieved from the Internet: URL:http://www.kuraray.eu/fileadmin/Downloads/mowiol/TDS_Mowiol_en_20110624.pdf [retrieved on May 23, 2014].
Le Laboratoire du Bain (France, http://www.laboudubain.com/).
M.K. Industries (Gujarat India, http://www.soapstrips.com).
Megulars Car Wash Strips: Megulars Inc. California, http://www.automotivedigesl.com/view_art.asp?articles!D=12414.
Michelle Villett, Why You Need a Sulfate-Free Shampoo, The Skincare Edit, updated date: Jan. 25, 2019, Original publication date: Feb. 22, 2016 (Year: 2016), 7 pages.
MOVA Pharmaceutical and Kosmos (USA, http:/lwww.icon-pr.com/news/news/prinl.cfm?inv_id=256-1).
Okasaka et al., "Evaluation of Anionic Surfactants Effects on The Skin Barrier Function Based on Skin Permeability", Pharmaceutical Development and Technology, vol. 24, No. 1, Jan. 23, 2018, pp. 99-104.
Product Review: Gemz Solid Shampoo, Travel as Much, published on Mar. 19, 2019, retrieved on Apr. 27, 2021, retrieved from the Internet URL: https://travelasmuch.com/gemz-solid-shampoo-review/.
Pure Soap Leafz: (Soap UNLTD. Netherlands, http://www.upandunder.com.uk/eshop/catalogue/testbs.asp?Manufacturer_ID=252&Activity_ID=33&Description_ID=157).
Sanipro Sanitary Products (Italy, http://www.sanipro.iit).
Solublon (Toyohashi Japan, http://www.solublon.com).
SPI Pharma (Delaware, http://www.spipharma.com).
Travelers Passport Paper Soap Sheets (http://www.weddingflavornow.com/index.asp?PageAction=VIEWPROD&PROD&ProdID=519).
Vaughan, C.D. "Solubility, Effects in Product, Package, Penetration and Preservation", Cosmetics and Toiletries, vol. 103, Oct. 1988.
Veslerby, A.: "Star volume in Bone Research: A Histomorphometric Analysis of Trabecular Bone Structure UsingVertical Sections", Anal Rec: Feb. 1993, 232(2), pp. 325-334.
Wenda (China, http://www.wenda.com).
Zhang et al. "Study on Morphology of Electrospun Poly( vinyl alcohol) Mats," European Polymer Journal 41 (2005), pp. 423-432.
U.S. Appl. No. 16/589,504, filed Oct. 1, 2019, Benson et al.
U.S. Appl. No. 15/981,096, filed May 16, 2018, Hamersky et al.
U.S. Appl. No. 16/912,876, filed Jun. 26, 2020, Song et al.
U.S. Appl. No. 29/672,822, filed Dec. 10, 2018, Tan et al.
U.S. Appl. No. 29/676,338, filed Jan. 10, 2019, Tan et al.
U.S. Appl. No. 29/728,687, filed Mar. 20, 2020, Cook et al.
U.S. Appl. No. 29/728,688, filed Mar. 20, 2020, Cook et al.
U.S. Appl. No. 29/707,807, filed Oct. 1, 2019, Washington et al.
U.S. Appl. No. 29/707,809, filed Oct. 1, 2019, Washington et al.
Dow, UCARE™ Polymer LR-400, Technical Data Sheet, Downloaded in Mar. 2022, 4 pages.
Karen Duis et al., "Environmental fate and effects of water-soluble synthetic organic polymers used in cosmetic products", Environmental Sciences Europe, vol. 33, Article No. 21, Feb. 16, 2021, 78 pages.
All Office Actions; U.S. Appl. No. 29/819,499, filed Dec. 15, 2021.
Color Keeper [online], [site visited Oct. 18, 2021]. Available from internet, URL: https://shopgemz.com/products/color-keeper?variant=13094595002434&utm_source=google&utm_medium=cpc&utm_campaign=Shopping&gclidCj0KCQjw5JSLBhCxARIsAHgO2SdAT7LTehpyxM1qTGtnFETDalNuo9_cQSOpPwCmsmmdGA1Y0USekQEaAh0iEALw_wCB (Year 2021).
Paper Pieces Hexagons, announced 2018 [online], [site visited Oct. 14, 2021]. Available from internet, URL:https://www.amazon.com/Paper-Pieces-HEX100B-Hexagons-1200pc/dp/B07DVYV2HN/ (Year: 2018).
Rounded hexagon shape, announced 2016 [online], [site visited Oct. 20, 2021], Available from internet, URL:https://www.vexels.com/png-svg/preview/139199/rounded-hexagon-shape (Year: 2016).
Ail Office Actions; U.S. Appl. No. 17/357,119, filed Jun. 24, 2021.
All Office Actions; U.S. Appl. No. 29/815,500, filed Nov. 15, 2021.
Raymond C Rowe et al., Polyvinyl Alcohol, Handbook of Pharmaceutical Excipients, 2009, Sixth Edition, Pharmaceutical Press, 564-565.
Sahin et al. "A Study on Physical and Chemical Properties of Cellulose Paper Immersed in Various Solvent Mixtures" International Journal of Molecular Sciences, Jan. 2008; 9(1): 78-88.
U.S. Appl. No. 29/819,499, filed Dec. 15, 2021, Sharonda Lee Crawford Washington et al.

FIBROUS STRUCTURES CONTAINING CATIONIC SURFACTANTS AND SOLUBLE ACIDS

FIELD OF THE INVENTION

The present invention relates to fibrous structures, more particularly to fibrous structures comprising a cationic surfactant, in particular a dimethyl amine, and an oil soluble acid.

BACKGROUND OF THE INVENTION

Most hair conditioner products in the market today are sold in liquid form. While widely used, liquid products often have tradeoffs in terms of packaging, storage, transportation, and/or convenience of use. It can be desirable to formulate conditioners as solid structures, including solid structures that are made from a plurality of fibers that quickly hydrate to form a consumer acceptable liquid hair conditioning product during use.

Even in fibrous structures, upon hydration the hair conditioner product can contain a gel network that is formed by a cationic surfactant, a high melting point fatty material, and the added water.

Some consumers, especially consumers who have fine hair, want an effective conditioner that also feels lightweight. These consumers may be particularly interested in conditioning products where the cationic surfactant can include a dimethyl amine, like stearamidopropyl dimethylamine and behenamidopropyl dimethylamine. These surfactants are not charged and in traditional liquid conditioners, it is common to add a water-soluble acid, like hydrochloric acid or citric acid, to acidify the surfactant, so it forms a gel network and provides effective conditioning.

However, when the conditioner product is a solid fibrous structure, it can be difficult to add acid. Fibrous structures can be formed by combining and heating fatty amphiphile(s), cationic surfactant(s), and polyvinyl structurant(s) until they form a molten homogenous melt. Some acids precipitate when added to the melt, instead of acidifying the surfactant to form a gel network with better conditioning. Other acids are not fully soluble in the melt, which causes the fibers to break during manufacturing, diminishing the structural integrity of the article.

As such, there remains a need for fibrous conditioner structures that can contain a dimethyl amine cationic surfactant and an acid that acidifies the surfactant and is soluble in the melt.

SUMMARY OF THE INVENTION

A fibrous structure comprising a plurality of fibrous elements comprising: (a) from about 1 wt % to about 50 wt % of a polymeric structurant having a weight average molecular weight of from about 10,000 to about 6,000,000 g/mol; (b) from about 10 wt % to about 85 wt % of a fatty material having a carbon chain length C12-C22 or mixtures thereof, wherein the melting point is above 25° C.; (c) from about 1 wt % to about 60 wt % of a cationic surfactant selected from the group consisting of a mono-long alkyl amine, a tertiary amine, and combinations thereof; (d) from about 0.1 wt. % to about 10 wt. % of an oil soluble acid selected from the group consisting of salicylic acid, lactic acid, acetic acid, malic acid, succinic acid, sorbic acid, 2,4-dihydroxybenzoic acid, maleic acid, and combinations thereof; wherein the oil soluble acid is dispersed throughout the fibrous elements.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

It can be desirable for conditioners to be articles containing fibrous structures containing filaments that upon adding water rapidly forms a solution or dispersion that can be easily applied to a user's hair.

Some consumers, especially consumers with fine hair want a conditioner that provides effective conditioning without weighing down hair. These consumers can be attracted to conditioners that contain a dimethyl amine cationic surfactant. However, these surfactants are not charged and without being acidified they are not incorporated as effectively into the gel network and the conditioner is less effective. In traditional liquid conditioners, a water-soluble acid, like citric acid or hydrochloric acid, is added to acidify the surfactants.

However, in the meltblowing and/or spunbonding processes, described hereafter, a water-soluble acid will not mix with the melt that contains fatty amphiphile(s), the cationic surfactant(s), and polyvinyl structurant(s). Instead of mixing, the water-soluble acid can form a separate phase in the melt. Some acids precipitate when added to the melt, instead of acidifying the surfactant to form a gel network with better conditioning. Other acids are not fully soluble in the melt, which causes the fibers to break during manufacturing, diminishing the structural integrity of the article.

Figure 1:
FIG. 1 is a photograph of a melt containing lactic acid.
Figure 2:
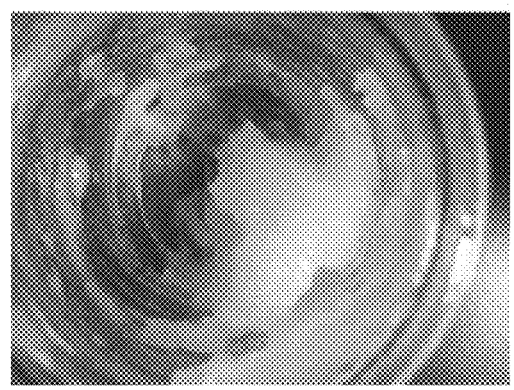
FIG. 2 is a photograph of a gel network formed from the melt in FIG. 1.

FIG. 1 is a photograph of an example melt containing, in part, lactic acid, fatty acid, and a dimethyl amine cationic surfactant. As shown in FIG. 1, the melt is one phase, clear, and homogenous, which indicates that the lactic acid is soluble in the melt composition. FIG. 2 is a photograph of a gel network that was formed when the composition of FIG. 1 is cooled. The gel network is viscous.

Figure 3:
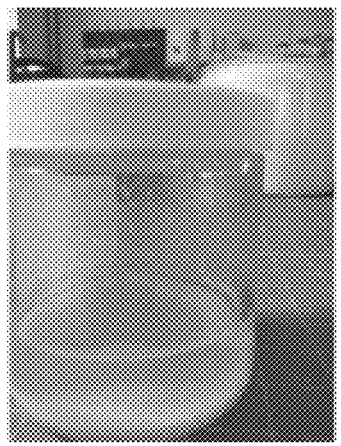
FIG. 3 is a photograph of a melt containing lactic acid.
Figure 4:
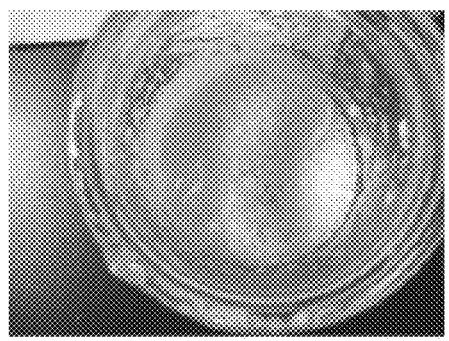
FIG. 4 is a photograph of a cooled version of the melt of FIG. 3.

FIG. 3 is a photograph of an example melt containing, in part, citric acid, fatty alcohol, and a dimethyl amine cationic surfactant. As shown in FIG. 3, the melt is two phases and contains particles, which indicates that the citric acid is not soluble in the composition. FIG. 4 is a photograph of the cooled composition of FIG. 3. The cooled composition does not form a gel network, instead it is a thin composition where one phase appears to float on top of the other.

In one example, the article can contain one or more particles as described in and WO2018140675A1, U.S. patent application Ser. No. 15/979,961, and U.S. Prov. App. No. 62/734,312, are hereby incorporated by reference.

Definitions

"Dissolvable" means that the Dissolvable Solid Structure is completely soluble in water or it provides a uniform dispersion upon mixing in water according to the Hand Dissolution Test, described hereafter. The Dissolvable Solid Structure can have a hand dissolution value of from about 1 to about 30 strokes, alternatively from about 2 to about 25 strokes, alternatively from about 3 to about 20 strokes, and alternatively from about 4 to about 15 strokes, as measured by the Hand Dissolution Method.

"Fibrous structure" as used herein means a structure that comprises one or more fibrous elements and optionally, one or more particles. In one example, a fibrous structure according to the present invention means an association of fibrous elements and optionally, particles that together form a structure, such as a unitary structure, capable of performing a function.

Figure 5:
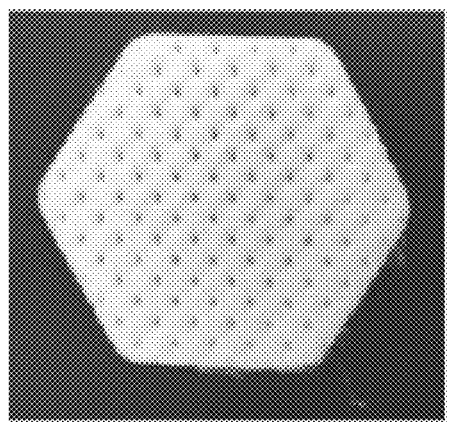
FIG. 5 is an example of a fibrous structure containing filaments.

FIG. 5 is an example of a fibrous structure containing filaments.

The fibrous structures of the present invention may be homogeneous or may be layered. If layered, the fibrous structures may comprise at least two and/or at least three and/or at least four and/or at least five layers. The layer can be fibrous elements, particles, and mixtures thereof.

In one example, the fibrous structure can be a multi-ply fibrous structure that exhibits a basis weight of less than 5000 g/m2 as measured according to the Basis Weight Test Method described herein.

In one example, the fibrous structure of the present invention can be a "unitary fibrous structure."

"Unitary fibrous structure" as used herein is an arrangement comprising a plurality of two or more and/or three or more fibrous elements that are inter-entangled or otherwise associated with one another to form a fibrous structure. The unitary fibrous structure can optionally contain particles. A unitary fibrous structure of the present invention may be one or more plies within a multi-ply fibrous structure. In one example, a unitary fibrous structure of the present invention may comprise three or more different fibrous elements. In another example, a unitary fibrous structure of the present invention may comprise two different fibrous elements, for example a co-formed fibrous structure, upon which a different fibrous element is deposited to form a fibrous structure comprising three or more different fibrous elements.

"Fibrous element" as used herein means an elongate particulate having a length greatly exceeding its average diameter, i.e. a length to average diameter ratio of at least about 10. A fibrous element may be a filament or a fiber. In one example, the fibrous element can be a single fibrous element rather than a yarn comprising a plurality of fibrous elements.

The fibrous elements of the present invention may be spun from a filament-forming composition also referred to as fibrous element-forming compositions via suitable spinning process operations, such as meltblowing, spunbonding, electro-spinning, and/or rotary spinning.

The fibrous elements of the present invention may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present invention and then cutting the filament or filament tow into segments of less than 5.08 cm (2 in.) thus producing fibers.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more polymeric structurants and one or more other ingredients, such as surfactants and high melting point fatty materials. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" and/or "fibrous element-forming composition" as used herein means a composition that can be suitable for making a fibrous element of the present invention such as by meltblowing and/or spunbonding. The filament-forming composition comprises one or more polymeric structurants that exhibit properties that make them suitable for spinning into a fibrous element. In addition, the filament-forming composition may comprise one or more polar solvents, such as water, into which one or more, for example all, of the polymeric structurant and/or one or more, for example all, of surfactants are dissolved and/or dispersed prior to spinning a fibrous element, such as a filament from the filament-forming composition.

Figure 6:
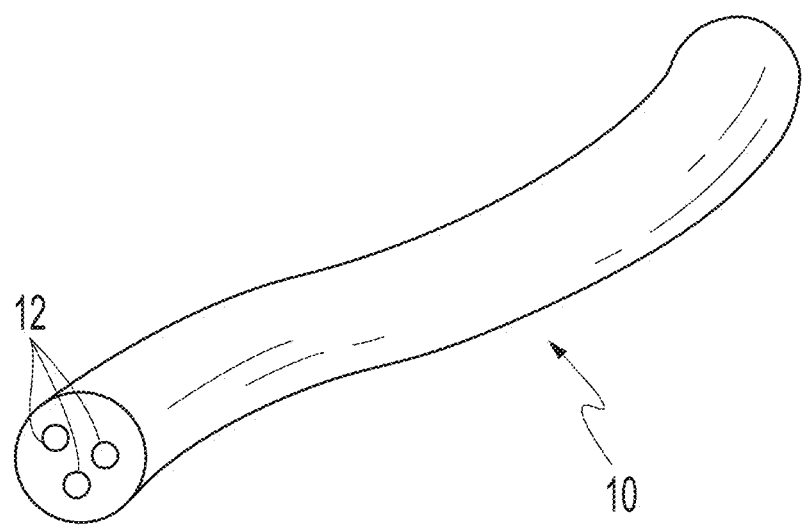
FIG. 6 is a schematic representation of an example of a fibrous element according to the present invention.

In one example, as shown in FIG. 6, a filament of the present invention made from a filament-forming composition of the present invention is such that one or more additives, for example one or more active agents, may be present in the filament rather than on the filament, such as a coating composition comprising one or more active agents, which may be the same or different from the active agents in the fibrous elements and/or particles.

In one example, one or more additives, such as active agents, may be present in the fibrous element and one or more additional additives, such as active agents, may be present on a surface of the fibrous element. In another example, a fibrous element of the present invention may comprise one or more additives, such as active agents, that are present in the fibrous element when originally made, but then bloom to a surface of the fibrous element prior to and/or when exposed to conditions of intended use of the fibrous element.

As used herein, "vinyl pyrrolidone copolymer" (and "copolymer" when used in reference thereto) refers to a polymer of the following structure (I):

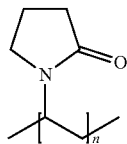

(I)

In structure (I), n is an integer such that the polymeric structurant has the degree of polymerization such that it possesses characteristics described herein. For purposes of clarity, the use of the term "copolymer" is intended to convey that the vinyl pyrrolidone monomer can be copolymerized with other non-limiting monomers such as vinyl acetate, alkylated vinyl pyrrolidone, vinyl caprolactam, vinyl valerolactam, vinyl imidazole, acrylic acid, methacrylate, acrylamide, methacrylamide, dimethacrylamide, alkylaminomethacrylate, and alkylaminomethacrylamide monomers.

As used herein, "vinyl acetate-vinyl alcohol copolymer" (and "copolymer" when used in reference thereto) refers to a polymer of the following structure (I):

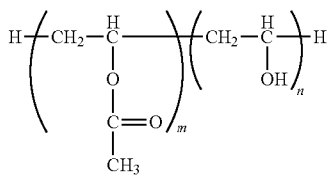

(I)

In structure (I), m and n are integers such that the polymeric structurant has the degree of polymerization and percent alcohol characteristics described herein. For purposes of clarity, this use of the term "copolymer" is intended to convey that the partially hydrolyzed polyvinyl acetate of the present invention comprises vinyl alcohol and vinyl acetate units. As discussed below, the polymeric structurant is routinely prepared by polymerizing vinyl acetate monomer followed by hydrolysis of some of the acetate groups to alcohol groups, as opposed to polymerization of vinyl acetate and vinyl alcohol monomer units (due in-part to the instability of vinyl alcohol).

"Conditions of intended use" as used herein means the temperature, physical, chemical, and/or mechanical conditions that a fibrous element and/or particle and/or fibrous structure of the present invention is exposed to when the fibrous element and/or particle and/or fibrous structure is used for one or more of its designed purposes. For instance, if a fibrous element and/or a particle and/or a fibrous structure comprising a fibrous element is designed to be used by a human as a shampoo for hair care purposes, the conditions of intended use will include those temperature, chemical, physical and/or mechanical conditions present during the shampooing of the human's hair. Likewise, if a fibrous element and/or a particle and/or a fibrous structure comprising a fibrous element is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active agent" as used herein means an additive that produces an intended effect in an environment external to a fibrous element and/or a particle and/or a fibrous structure comprising a fibrous element of the present invention, such as when the fibrous element and/or a particle and/or fibrous structure is exposed to conditions of intended use of the fibrous element and/or a particle and/or a fibrous structure comprising a fibrous element. In one example, an active agent comprises an additive that treats a surface, including a soft surface (i.e., hair, skin). In another example, an active agent comprises an additive that creates a chemical reaction (i.e., foaming, fizzing, coloring, warming, cooling, lathering, disinfecting and/or clarifying and/or chlorinating, such as in clarifying water and/or disinfecting water and/or chlorinating water). In yet another example, an active agent comprises an additive that treats an environment (i.e., deodorizes, purifies, perfumes). In one example, the active agent is formed in situ, such as during the formation of the fibrous element and/or particle containing the active agent, for example the fibrous element and/or particle may comprise a water-soluble polymer (e.g., starch) and/or a surfactant (e.g., anionic surfactant), which may create a polymer complex or coacervate that functions as the active agent used to treat the hair and/or scalp.

"Treats" as used herein with respect to treating a surface means that the active agent provides a benefit to a surface or environment. Treats includes regulating and/or immediately improving a surface's, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

"Weight ratio" as used herein means the ratio between two materials on their dry basis.

"Water-soluble material" as used herein means a material that is miscible in water. In other words, a material that is capable of forming a stable (does not separate for greater than 5 minutes after forming the homogeneous solution) homogeneous solution with water at ambient conditions.

"Water-insoluble" as used herein is meant that the material, particle, and/or substrate does not dissolve in or readily break apart upon immersion in water. In some instances, water-insoluble materials swell when exposed to water.

"Ambient conditions" as used herein means 23° C.±1.0° C. and a relative humidity of 50%±2%.

As used herein, "molecular weight" or "M·Wt." refers to the weight average molecular weight unless otherwise stated. Molecular weight is measured using industry standard method, gel permeation chromatography ("GPC").

"Length" as used herein, with respect to a fibrous element, means the length along the longest axis of the fibrous element from one terminus to the other terminus. If a fibrous element has a kink, curl or curves in it, then the length is the length along the entire path of the fibrous element from one terminus to the other terminus.

"Diameter" as used herein, with respect to a fibrous element, is measured according to the Diameter Test Method described herein. In one example, a fibrous element of the present invention exhibits a diameter of less than 100 µm and/or less than 75 µm and/or less than 50 µm and/or less than 25 µm and/or less than 20 µm and/or less than 15 µm and/or less than 10 µm and/or less than 6 µm and/or greater than 1 µm and/or greater than 3 µm.

"Triggering condition" as used herein in one example means anything, as an act or event, that serves as a stimulus and initiates or precipitates a change in the fibrous element and/or particle and/or fibrous structure of the present invention, such as a loss or altering of the fibrous element's and/or fibrous structure's physical structure and/or a release of an additive, such as an active agent therefrom. In another example, the triggering condition may be present in an environment, such as water, when a fibrous element and/or particle and/or fibrous structure of the present invention is added to the water. In other words, nothing changes in the water except for the fact that the fibrous element and/or fibrous structure of the present invention is added to the water.

"Morphology changes" as used herein with respect to a fibrous element's and/or particle's morphology changing means that the fibrous element experiences a change in its physical structure. Non-limiting examples of morphology changes for a fibrous element and/or particle of the present invention include dissolution, melting, swelling, shrinking, breaking into pieces, exploding, lengthening, shortening, and combinations thereof. The fibrous elements and/or particles of the present invention may completely or substantially lose their fibrous element or particle physical structure or they may have their morphology changed or they may retain or substantially retain their fibrous element or particle physical structure as they are exposed to conditions of intended use.

"By weight on a dry fibrous element basis" and/or "by weight on a dry fibrous structure basis" means the weight of the fibrous element and/or particle and/or fibrous structure, respectively, measured immediately after the fibrous element and/or particle and/or fibrous structure, respectively, has been conditioned in a conditioned room at a temperature of 23° C.±1.0° C. and a relative humidity of 50%±10% for 2 hours. In one example, by weight on a dry fibrous element basis and/or dry fibrous structure basis means that the fibrous element and/or particle and/or fibrous structure comprises less than 20% and/or less than 15% and/or less than 10% and/or less than 7% and/or less than 5% and/or less than 3% and/or to 0% and/or to greater than 0% based on the dry weight of the fibrous element and/or particle and/or fibrous structure of moisture, such as water, for example free water, as measured according to the Water Content Test Method described herein.

"Total level" as used herein, for example with respect to the total level of one or more active agents present in the fibrous element and/or particle and/or fibrous structure, means the sum of the weights or weight percent of all of the subject materials, for example active agents. In other words, a fibrous element and/or particle and/or fibrous structure may comprise 25% by weight on a dry fibrous element basis and/or dry fibrous structure basis of an anionic surfactant, 15% by weight on a dry fibrous element basis and/or dry fibrous structure basis of a nonionic surfactant, 10% by weight of a chelant on a dry fibrous element basis and/or dry fibrous structure basis, and 5% by weight of a perfume a dry fibrous element basis and/or dry fibrous structure basis so that the total level of active agents present in the fibrous element and/or particle and/or fibrous structure is greater than 50%; namely 55% by weight on a dry fibrous element basis and/or dry fibrous structure basis.

"Fibrous structure product" as used herein means a solid form, for example a rectangular solid, sometimes referred to as a sheet, that comprises one or more active agents, for example a fabric care active agent, a dishwashing active agent, a hard surface active agent, and mixtures thereof. In one example, a fibrous structure product of the present invention comprises one or more surfactants, one or more enzymes (such as in the form of an enzyme prill), one or more perfumes and/or one or more suds suppressors. In another example, a fibrous structure product of the present invention comprises a builder and/or a chelating agent. In another example, a fibrous structure product of the present invention comprises a bleaching agent (such as an encapsulated bleaching agent).

"Associate," "Associated," "Association," and/or "Associating" as used herein with respect to fibrous elements and/or particle means combining, either in direct contact or in indirect contact, fibrous elements and/or particles such that a fibrous structure is formed. In one example, the associated fibrous elements and/or particles may be bonded together for example by adhesives and/or thermal bonds. In another example, the fibrous elements and/or particles may be associated with one another by being deposited onto the same fibrous structure making belt and/or patterned belt.

"Ply" or "Plies" as used herein means an individual fibrous structure optionally to be disposed in a substantially contiguous, face-to-face relationship with other plies, forming a multiple ply fibrous structure. It is also contemplated that a single fibrous structure can effectively form two "plies" or multiple "plies", for example, by being folded on itself.

As used herein, the articles "a" and "an" when used herein, for example, "an anionic surfactant" or "a fiber" is understood to mean one or more of the material that is claimed or described.

As used herein, the terms "include," "includes," and "including," are meant to be non-limiting.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise noted, all component or composition levels are in reference to the active level of that component or composition, and are exclusive of impurities, for example, residual solvents or by-products, which may be present in commercially available sources.

Fibrous Structure

The fibrous structure of the present invention can comprise a plurality of fibrous elements, for example a plurality of filaments.

The fibrous structure can include: fibrous elements containing (a) from about 1 wt. % to about 50 wt % polymeric structurant; (b) from about 10 wt. % to about 85 wt. % of a high melting point fatty material such as a fatty amphiphile, (c) from about 1 wt. % to about 60 wt. % of a cationic surfactant; and (d) from about 0.1-10% an oil soluble acid. When water is added to the fibrous structure at a ratio of about 10:1 a lamellar structure can be formed.

FIG. 5 shows a fibrous structure according to the present invention. The fibrous structure comprises a plurality of fibrous elements, in this case filaments. The filaments contain the polymeric structurant, high melting point fatty material, the cationic surfactant, and the oil soluble acid. The polymeric structurant, high melting point fatty material, the cationic surfactant, and/or oil soluble acid can be dispersed throughout the filament. The filament can be homogenous. In some examples, the oil soluble acid may not be present in a coating that is applied to the fibrous structure and/or the filaments. In other examples, the oil soluble acid may not be present in particles that are incorporated into or sprayed onto of the fibrous structure.

Even though the fibrous element and/or fibrous structure of the present invention are in solid form, the filament-forming composition used to make the fibrous elements of the present invention may be in the form of a liquid.

In one example, the fibrous structure comprises a plurality of identical or substantially identical from a compositional perspective of fibrous elements according to the present invention.

In another example, the fibrous structure may comprise two or more different fibrous elements according to the present invention. Non-limiting examples of differences in the fibrous elements may be physical differences such as differences in diameter, length, texture, shape, rigidness, elasticity, and the like; chemical differences such as cross-linking level, solubility, melting point, Tg, active agent, polymeric structurant, color, level of active agent, basis weight, level of polymeric structurant, presence of any coating on fibrous element, biodegradable or not, hydrophobic or not, contact angle, and the like; differences in whether the fibrous element loses its physical structure when the fibrous element is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use. In one example, two or more fibrous elements and/or particles within the fibrous structure may comprise different active agents. This may be the case where the different active agents may be incompatible with one another, for example an anionic surfactant (such as a shampoo active agent) and a cationic surfactant (such as a hair conditioner active agent).

In another example, the fibrous structure may exhibit different regions, such as different regions of basis weight, density and/or caliper. In yet another example, the fibrous structure may comprise texture on one or more of its surfaces. A surface of the fibrous structure may comprise a pattern, such as a non-random, repeating pattern. The fibrous structure may be embossed with an emboss pattern. In another example, the fibrous structure may comprise apertures. The apertures may be arranged in a non-random, repeating pattern.

The fibrous structure of the present invention may be used as is or may be coated with one or more active agents.

In one example, the fibrous structure of the present invention exhibits a thickness of greater than 0.01 mm and/or greater than 0.05 mm and/or greater than 0.1 mm and/or to about 100 mm and/or to about 50 mm and/or to about 20 mm and/or to about 10 mm and/or to about 5 mm and/or to about 2 mm and/or to about 0.5 mm and/or to about 0.3 mm as measured by the Thickness Test Method described herein.

The fibrous structure can be a hair conditioner structure. Alternatively, the cationic polymers can be combined with anionic polymers to form a combination hair shampoo and conditioner structure.

For fibrous structures, the structure can comprise a significant number of dissolvable fibers with an average diameter less than about 150 micron, alternatively less than about 100 micron, alternatively less than about 10 micron, and alternatively less than about 1 micron with a relative standard deviation of less than 100%, alternatively less than 80%, alternatively less than 60%, alternatively less than 50%, such as in the range of 10% to 50%, for example. As set forth herein, the significant number means at least 10% of all the dissolvable fibers, alternatively at least 25% of all the dissolvable fibers, alternatively at least 50% of all the dissolvable fibers, alternatively at least 75% of all the dissolvable fibers. The significant number may be at least 99% of all the dissolvable fibers. Alternatively, from about 50% to about 100% of all the dissolvable fibers may have an average diameter less than about 10 micron. The dissolvable fibers produced by the method of the present disclosure can have a significant number of dissolvable fibers with an average diameter less than about 1 micron, or sub-micron fibers. In an embodiment, fibrous structure may have from about 25% to about 100% of all the dissolvable fibers with an average diameter less than about 1 micron, alternatively from about 35% to about 100% of all the dissolvable fibers with an average diameter less than about 1 micron, alternatively from about 50% to about 100% of all the dissolvable fibers with an average diameter less than about 1 micron, and alternatively from about 75% to about 100% of all the dissolvable fibers with an average diameter less than about 1 micron.

The structure can be characterized in one aspect by its Specific Surface Area. The structure can have a Specific Surface Area of from about 0.03 m/g to about 0.25 m/g, alternatively from about 0.035 $m^2/g$ to about 0.22 $m^2/g$, alternatively from about 0.04 $m^2/g$ to about 0.19 $m^2/g$, and alternatively from about 0.045 $m^2/g$ to about 0.16 $m^2/g$.

The structure can be a flat, flexible structure in the form of a pad, a strip, or tape and having a thickness of from about 0.5 mm to about 10 mm, alternatively from about 1 mm to about 9 mm, alternatively from about 2 mm to about 8 mm, and alternatively from about 3 mm to about 7 mm as measured by the below methodology. The Structure can be a sheet having a thickness from about 5 mm to about 6.5 mm. Alternatively, two or more sheets are combined to form a Structure with a thickness of about 5 mm to about 10 mm.

The structure can have a basis weight of from about 200 grams/m² to about 2,000 grams/m², alternatively from about 400 g/m² to about 1,200 g/m², alternatively from about 600 g/m² to about 2,000 g/m², and alternatively from about 700 g/m² to about 1,500 g/m².

The structure can have a dry density of from about 0.08 g/cm³ to about 0.40 g/cm³, alternatively from about 0.08 g/cm³ to about 0.38 g/cm³, alternatively from about 0.10 g/cm³ to about 0.25 g/cm³, and alternatively from about 0.12 g/cm³ to about 0.20 g/cm³.

Non-limiting examples of other fibrous structures suitable for the present invention are disclosed in U.S. Pat. Nos. 8,980,816 and 9,139,802 and U.S. Pub. No. 2013/0171421 are hereby incorporated by reference.

Fibrous Elements

The fibrous element, such as a filament and/or fiber, of the present invention comprises one or more polymeric structurants. In addition to the polymeric structurants, the fibrous element may further comprise one or more high melting point fatty materials, one or more cationic surfactants, one or more oil soluble acids and optional ingredients. Examples of fibrous elements can be found at U.S. patent application Ser. No. 15/979,961, incorporated by reference.

Polymeric Structurant

To improve the fiber spinning of low viscosity material, such as molten fatty alcohols, fatty quaternary ammonium compounds, fatty acids, etc., a polymeric ingredient called a structurant can be added. The structurant increases the shear and extensional viscosity of the fluid to enable fiber formation. The structurant can be included at a level of from about 1 wt. % to about 50 wt. %, alternatively from about 1 wt. % to about 30 wt. %, alternatively from about 1 wt. % to about 10 wt. %, alternatively from about 2 wt. % to about 6 wt. %, and alternatively from about 3 wt. % to about 5 wt. % of the composition. The structurant has a weight average molecular weight of from about 10,000 to about 6,000,000 g/mol. A balance can be struck between concentration and molecular weight, such that when a lower molecular weight species is used, it requires a higher level to result in optimal fiber spinning. Likewise, when a higher molecular species is used, lower levels can be used to achieve optimal fiber spinning. The structurant having a weight average molecular weight of from about 3,000,000 g/mol to about 5,000,000 g/mol in included at a level of from about 3 wt. % to about 6 wt. %. Alternatively, a structurant having a weight average molecular weight of from about 50,000 g/mol to about 100,000 g/mol can be included at a level of from about 30 wt. % to about 50 wt. %.

The structurant can be soluble in an oily mixture to enable viscosity build for fiber spinning. In addition, the structurant should also be soluble in water to promote removal and to prevent buildup. Suitable structurants include, but are not limited to, polyvinylpyrrolidone, polydimethylacrylamides, and combinations thereof. These polymers are oil (fatty alcohol, fatty acid, fatty quaternary ammonium compounds) soluble, water soluble, and capable of being produced at high weight average molecular weights. For example, suitable polymers for use are PVP K120 from Ashland Inc., having a weight average molecular weight of about 3,500,000 g/mol is soluble in the oil and water and enables fibers to be formed and collected onto a belt. Additional suitable polymers include copolymers of polyvinylpyrrolidone, such as Ganex® or PVP/VA (weight average molecular weight of about 50,000 g/mol) copolymers from Ashland Inc., also performed as suitable structurants but a higher level was utilized to be effective due to their lower weight average molecular weight. In addition, copolymers of polydimethylacrylamide also function as a suitable structurant. Hydroxyl propyl cellulose can also function as a suitable structurant.

Dispersing Agents

The fibrous elements, it has been found that the addition of a dispersing agent can greatly increase the wetting, hydration, and dispersion of the conditioner materials. The dispersing agent can be included at a level of from about 1 wt. % to about 30 wt. % of the composition, alternatively from about 5 wt. % to about 15 wt. %, and alternatively from about 5 wt. % to about 10 wt %. A surfactant from the nonionic class of alkyl glucamides can improve the wetting and hydration when added to the solid conditioner formula. The alkyl glucamide surfactant contains a hydrophobic tail of about 8-18 carbons and a nonionic head group of glucamide. For glucamide, the presence of the amide and hydroxyl groups may provide sufficient polarity that balances the hydrophobic carbon tail in such a way to permit the surfactant's solubility in the conditioner oils and also imparts a rapid dispersion of the conditioner ingredients upon exposure to water. Other similar dispersing agents include, but are not limited to, reverse alkyl glucamides, cocoamiodpropyl betaines, alkyl glucoside, Triethanol amine, cocamide MEAs and mixtures thereof.

Cationic Surfactant

The fibrous element can contain a cationic surfactant can be included at a level of from about 1 wt. % to about 60 wt. %, alternatively from about 10 wt. % to about 50 wt. %, alternatively from about 20 wt. % to about 40 wt. % of the composition. Cationic surfactant useful herein can be one cationic surfactant or a mixture of two or more cationic surfactants. The cationic surfactant can be selected from the group consisting of, but not limited to: a mono-long alkyl amine, a tertiary amine, and combinations thereof.

The fibrous structure can also contain cationic surfactants including a mono-long alkyl quaternized ammonium salt; a combination of a mono-long alkyl quaternized ammonium salt and a di-long alkyl quaternized ammonium salt; a combination of a mono-long alkyl amine and a di-long alkyl quaternized ammonium salt; and a combination of a mono-long alkyl amine and a mono-long alkyl quaternized ammonium salt, a tertiary amine and combinations thereof. In these examples, the surfactant is quaternized and can form a gel network without the addition of acid. However, it can be advantageous to add the oil soluble acids, as described herein, to help adjust the pH.

Mono-Ion Alkyl Amine

Mono-long alkyl amine useful herein are those having one long alkyl chain of from 12 to 30 carbon atoms, alternatively from 16 to 24 carbon atoms, alternatively from 18 to 22 carbon atoms. Mono-long alkyl amines useful herein also include mono-long alkyl amidoamines. Primary, secondary, and tertiary fatty amines are useful.

Tertiary amido amines having an alkyl group of from about 12 to about 22 carbons can be used in the fibrous elements. Exemplary tertiary amido amines include: stearamidopropyl dimethylamine, stearamidopropyl diethylamine, stearamidoethyl diethylamine, stearamidoethyl dimethylamine, palmitamido propyldimethylamine, palmitamidopropyldiethylamine, palmitamidoethyldiethylamine, palmitamidoethyldimethylamine, behenamidopropyldimethylamine, behenamidopropyl diethylamine, behenamidoethyl diethylamine, behenamido ethyldimethylamine, arachid amidopropyl dimethylamine, arachid amidopropyl diethylamine, arachid amidoethyl diethylamine, arachid amidoethyl dimethylamine, diethylaminoethyl stearamide. Useful amines in the present invention are disclosed in U.S. Pat. No. 4,275,055, Nachtigal, et al.

Oil Soluble Acid

The fibrous elements can contain from about 0.01 wt. % to 10 wt. % oil soluble acid, alternatively from about 0.1 wt. % to about 9 wt. %, alternatively about 0.25 wt. % to about 7 wt. %, alternatively from about 0.3 wt. % to about 5 wt. %.

The acid can be an oil soluble acid. If the acid is not soluble in the melt, then the melt cannot be spun because the melt is not homogenous, which, for example, can the fibrous structures to break during spinning and/or clog the die.

The mono-long alkyl amine can be used in combination with oil soluble acids such as salicylic acid, lactic acid, acetic acid, malic acid, succinic acid, sorbic acid, 2,4-dihydroxybenzoic acid, maleic acid. In one example, the filaments can be substantially free of or free of t-glutamic acid, fumaric acid, tartaric acid, citric acid, t-glutamic hydrochloride, citric acid, and mixtures thereof. A molar ratio of the amine to the acid of from about 1:0.3 to about 1:2, alternatively from about 1:0.4 to about 1:1.

In some examples, the fibrous elements are free of or substantially free of hydrochloric acid, citric acid, and combinations thereof. "Substantially free" of hydrochloric acid, citric acid, and combinations thereof means less than 0.05 wt. %, less than 0.04 wt. %, less than 0.03 wt. %, less than 0.02 wt. %, and/or less than 0.01 wt. %.

High Melting Point Fatty Material

The fibrous element can contain one or more high melting point fatty materials. The high melting point fatty material can be included at a level of from about 10 wt. % to about 85 wt. %, alternatively from about 20 wt. % to about 70 wt. %, alternatively from about 50 wt. % to about 70 wt. %, alternatively from about 10 wt. % to about 20 wt. % of the composition. The fatty material can be selected from the group consisting of, but not limited to, fatty amphiphiles, fatty alcohol, fatty acid, fatty amide, fatty ester and combinations thereof.

The high melting point fatty material useful herein can have a melting point of 25° C. or higher, alternatively 40° C. or higher, alternatively 45° C. or higher, alternatively 50° C. or higher, in view of stability of the emulsion especially the gel matrix. Such melting point is up to about 90° C., alternatively up to about 80° C., alternatively up to about 70° C., alternatively up to about 65° C., in view of easier manufacturing and easier emulsification. The high melting point fatty material can be used as a single compound or as a blend or mixture of at least two high melting point fatty material. When used as such blend or mixture, the above melting point means the melting point of the blend or mixture.

The high melting point fatty material useful herein can be selected from the group consisting of fatty alcohols, fatty acids, fatty alcohol derivatives, fatty acid derivatives, fatty amides, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound but is done so for convenience of classification and nomenclature. Further, it is understood by the artisan that, depending on the number and position of double bonds, and length and position of the branches, certain compounds having certain required carbon atoms may have a melting point of less than the above. Such compounds of low melting point are not intended to be included in this section. Non-limiting examples of the high melting point materials are found in International Cosmetic Ingredient Dictionary, Fifth Edition, 1993, and CTFA Cosmetic Ingredient Handbook, Second Edition, 1992.

Among a variety of high melting point fatty materials, fatty alcohols can be used in the composition described herein. The fatty alcohols useful herein are those having from about 14 to about 30 carbon atoms, alternatively from about 16 to about 22 carbon atoms. These fatty alcohols are saturated and can be straight or branched chain alcohols.

Suitable fatty alcohols include, but are not limited to, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

Generally, in the mixture, the weight ratio of cetyl alcohol to stearyl alcohol is from about 1:9 to 9:1, alternatively from about 1:4 to about 4:1, alternatively from about 1:2.3 to about 1.5:1.

When using higher level of total cationic surfactant and high melting point fatty materials, the mixture has the weight ratio of cetyl alcohol to stearyl alcohol of from about 1:1 to about 4:1, alternatively from about 1:1 to about 2:1, alternatively from about 1.2:1 to about 2:1, in view of maintaining acceptable consumer usage. It may also provide more conditioning on damaged part of the hair.

Extensional Aids

The fibrous elements can contain extensional aids. Non-limiting examples of extensional aids can include polymers, other extensional aids, and combinations thereof.

In one example, the extensional aids have a weight-average molecular weight of at least about 500,000 Da. The weight average molecular weight of the extensional aid is from about 500,000 Da to about 25,000,000 Da, alternatively from about 800,000 Da to about 22,000,000 Da, alternatively from about 1,000,000 Da to about 20,000,000 Da, and alternatively from about 2,000,000 Da to about 15,000,000 Da. The high molecular weight extensional aids are preferred in some examples of the invention due to the ability to increase extensional melt viscosity and reducing melt fracture.

The extensional aid, when used in a meltblowing process, can be added to the composition of the present invention in an amount effective to visibly reduce the melt fracture and capillary breakage of fibers during the spinning process such that substantially continuous fibers having relatively consistent diameter can be melt spun. Regardless of the process employed to produce fibrous elements and/or particles, the extensional aids, when used, can be present from about 0.001% to about 10%, by weight on a dry fibrous element basis and/or dry fibrous structure basis, in one example, and in another example from about 0.005 to about 5%, by weight on a dry fibrous element basis and/or dry fibrous structure basis, in yet another example from about 0.01 to about 1%, by weight on a dry fibrous element basis and/or dry fibrous structure basis, and in another example from about 0.05% to about 0.5%, by weight on a dry fibrous element basis and/or dry fibrous structure basis.

Non-limiting examples of polymers that can be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include modified and unmodified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Optional Ingredients

The structure optionally comprises from about 1 wt. % to about 25 wt. % plasticizer, in one embodiment from about 3 wt % to about 20 wt. % plasticizer, in one embodiment from about 5 wt. % to about 15 wt. % plasticizer.

When present in the structures, non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol, isosorbide, glucamine, N-methylglucamine and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

EP 0283165 B1 discloses suitable plasticizers, including glycerol derivatives such as propoxylated glycerol.

The Structure may comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials. Further non-limiting examples of optional ingredients include encapsulated perfumes, such as by β-cyclodetrins, polymer microcapsules, starch encapsulated accords and combinations thereof.

Suitable conditioning agents include high melting point fatty materials, silicone conditioning agents and cationic conditioning polymers. Suitable materials are discussed in US 2008/0019935, US 2008/0242584 and US 2006/0217288.

Methods of Use

The compositions described herein may be used for cleaning, condition, and/or treating hair, hair follicles, and/or skin including the scalp. The method for treating these consumer substrates may comprise the steps of: a) applying an effective amount of the structure to the hand, b) wetting the structure with water to dissolve the solid, c) applying the dissolved material to the target consumer substrate such as to clean, condition, or treat it, and d) rinsing the diluted treatment composition from the consumer substrate. These steps can be repeated as many times as desired to achieve the desired cleansing and or treatment benefit. When the structure is a conditioner, it can be applied before and/or after and/or concurrently with a shampoo.

A method useful for providing a benefit to hair, hair follicles, and/or skin including the scalp, includes the step of applying a composition according to the first embodiment to these target consumer substrates in need of regulating.

Alternatively, a useful method for regulating the condition of hair, hair follicles, skin, and/or skin including the scalp, includes the step of applying one or more compositions described herein to these target consumer substrates in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams, alternatively from about 1.0 grams to about 5 grams, and alternatively from about 1.5 grams to about 3 grams.

Product Types and Articles of Commerce

Non-limiting examples of products that utilize the fibrous structure include hand cleansing substrates, hair shampoo, hair conditioner or other hair treatment substrates, body cleansing substrates, shaving preparation substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

Described herein is an article of commerce comprising one or more fibrous structures described herein, and a communication directing a consumer to dissolve the Structure and apply the dissolved mixture to hair, hair follicles, skin including the scalp, to achieve a benefit to the target consumer substrate, a rapidly lathering foam, a rapidly rinsing foam, a clean rinsing foam, a conditioning treatment and combinations thereof. The communication may be printed material attached directly or indirectly to packaging that contains the fibrous structure or on the fibrous structure itself. Alternatively, the communication may be an electronic or a broadcast message that is associated with the article of manufacture. Alternatively, the communication may describe at least one possible use, capability, distinguishing feature and/or property of the article of manufacture.

Exposure to Triggering Condition

The conditioning ingredients, including the cationic surfactant and fatty alcohol, may be released from the fibrous element and/or fibrous structure when the fibrous element and/or fibrous structure is exposed to a triggering condition. In one example, one or more active agents may be released from the fibrous element and/or fibrous structure or a part thereof when the fibrous element and/or fibrous structure or the part thereof loses its identity, in other words, loses its physical structure. For example, a fibrous element and/or fibrous structure loses its physical structure when the polymeric structurant dissolves, melts or undergoes some other transformative step such that its structure is lost. In one example, the one or more active agents are released from the fibrous element and/or fibrous structure when the fibrous element's and/or fibrous structure's morphology changes.

In another example, one or more active agents may be released from the fibrous element and/or fibrous structure or a part thereof when the fibrous element and/or fibrous structure or the part thereof alters its identity, in other words, alters its physical structure rather than loses its physical structure. For example, a fibrous element and/or fibrous structure alters its physical structure when the polymeric structurant swells, shrinks, lengthens, and/or shortens, but retains its filament-forming properties.

In another example, one or more active agents may be released from the fibrous element and/or fibrous structure with its morphology not changing (not losing or altering its physical structure).

In one example, the fibrous element and/or fibrous structure may release an active agent upon the fibrous element and/or fibrous structure being exposed to a triggering condition that results in the release of the active agent, such as by causing the fibrous element and/or fibrous structure to lose or alter its identity as discussed above. Non-limiting examples of triggering conditions include exposing the fibrous element and/or fibrous structure to solvent, a polar solvent, such as alcohol and/or water, and/or a non-polar solvent, which may be sequential, depending upon whether the filament-forming composition comprises a polar solvent-soluble material and/or a non-polar solvent-soluble material; exposing the fibrous element and/or particle and/or fibrous structure to heat, such as to a temperature of greater than 75° F. and/or greater than 100° F. and/or greater than 150° F. and/or greater than 200° F. and/or greater than 212° F.; exposing the fibrous element and/or particle and/or fibrous structure to cold, such as to a temperature of less than 40° F. and/or less than 32° and/or less than 0° F.; exposing the fibrous element and/or fibrous structure to a force, such as a stretching force applied by a consumer using the fibrous element and/or fibrous structure; and/or exposing the fibrous element and/or fibrous structure to a chemical reaction; exposing the fibrous element and/or fibrous structure to a condition that results in a phase change; exposing the fibrous element and/or fibrous structure to a pH change and/or a pressure change and/or temperature change; exposing the fibrous element and/or fibrous structure to one or more chemicals that result in the fibrous element and/or fibrous structure releasing one or more of its active agents; exposing the fibrous element and/or particle and/or fibrous structure to ultrasonics; exposing the fibrous element and/or fibrous structure to light and/or certain wavelengths; exposing the fibrous element and/or fibrous structure to a different ionic strength; and/or exposing the fibrous element and/or fibrous structure to an active agent released from another fibrous element and/or fibrous structure.

In one example, one or more active agents may be released from the fibrous elements of the present invention when a fibrous structure product comprising the fibrous elements is subjected to a triggering step such as forming a wash liquor by contacting the fibrous structure product with water.

Method for Making Fibrous Elements

The fibrous elements of the present invention may be made by any suitable process. A non-limiting example of a suitable process for making the fibrous elements is described below.

Figure 7:
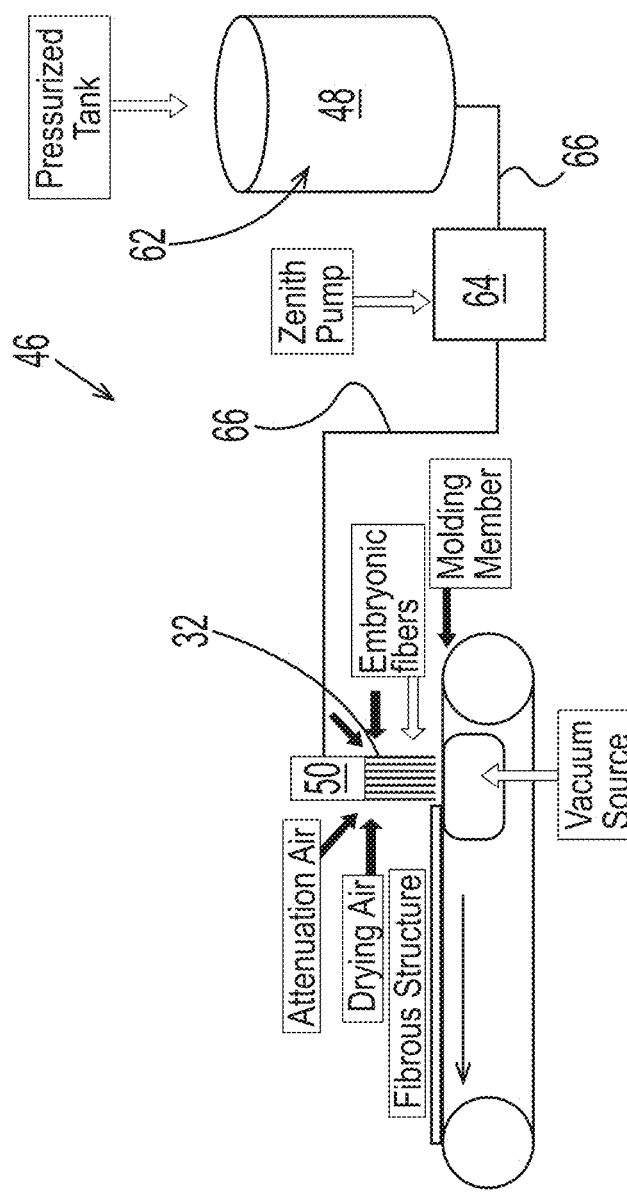
FIG. 7 is a schematic representation of an example of a process for making fibrous elements of the present invention.
Figure 8:
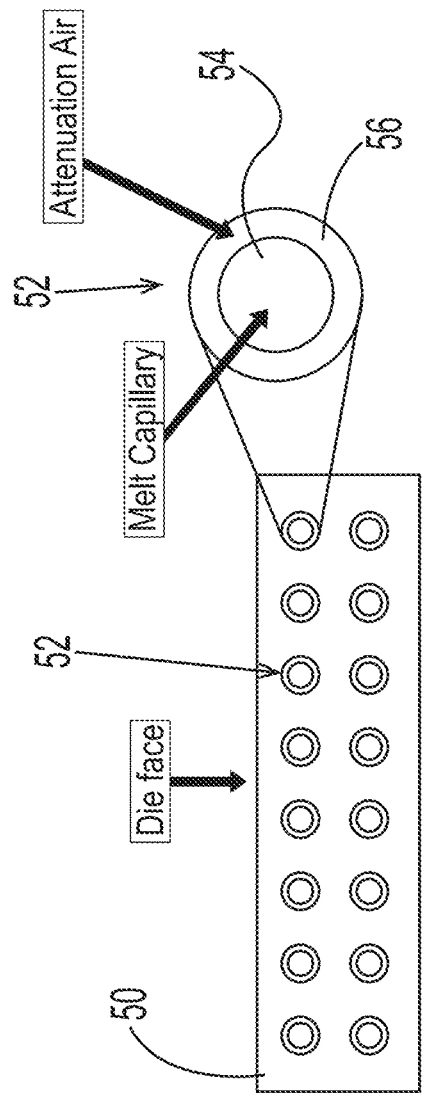
FIG. 8 is a schematic representation of an example of a die with a magnified view used in the process of FIG. 7.

In one example, as shown in FIGS. 7 and 8 a method 46 for making a fibrous element 32 according to the present invention comprises the steps of:

a. providing a filament-forming composition 48 comprising one or polymeric structurants, and optionally one or more other ingredients including high melting point fatty materials and/or one or more surfactants; and b. spinning the filament-forming composition 48, such as via a spinning die 50, into one or more fibrous elements 32, such as filaments, comprising the one or more polymeric structurants and optionally, the one or more other ingredients. The one or more other ingredients may be releasable from the fibrous element when exposed to conditions of intended use. The total level of the one or more polymeric structurants present in the fibrous element 32, may be less than 80% and/or less than 70% and/or less than 65% and/or 50% or less by weight on a dry fibrous element basis and/or dry fibrous structure basis and the total level of the one or more active agents, when present in the fibrous element may be greater than 20% and/or greater than 35% and/or 50% or greater 65% or greater and/or 80% or greater by weight on a dry fibrous element basis and/or dry fibrous structure basis.

As shown in FIG. 8, the spinning die 50 may comprise a plurality of fibrous element-forming holes 52 that include a melt capillary 54 encircled by a concentric attenuation fluid hole 56 through which a fluid, such as air, passes to facilitate attenuation of the filament-forming composition 48 into a fibrous element 32 as it exits the fibrous element-forming hole 52.

In one example, during the spinning step, any volatile solvent, such as water, present in the filament-forming composition 48 is removed, such as by drying, as the fibrous element 32 is formed. In one example, greater than 30% and/or greater than 40% and/or greater than 50% of the weight of the filament-forming composition's volatile solvent, such as water, is removed during the spinning step, such as by drying the fibrous element being produced.

The filament-forming composition may comprise any suitable total level of polymeric structurant and any suitable level of active agents so long as the fibrous element produced from the filament-forming composition comprises a total level of polymeric structurant in the fibrous element of from about 5% to 50% or less by weight on a dry fibrous element basis and/or dry fibrous structure basis and a total level of active agents in the fibrous element of from 50% to about 95% by weight on a dry fibrous element basis and/or dry fibrous structure basis.

In one example, the filament-forming composition may comprise any suitable total level of polymeric structurant and any suitable level of active agents so long as the fibrous element produced from the filament-forming composition comprises a total level of polymeric structurant in the fibrous element and/or particle of from about 5% to 50% or less by weight on a dry fibrous element basis and/or dry fibrous structure basis and a total level of active agents in the fibrous element and/or particle of from 50% to about 95% by weight on a dry fibrous element basis and/or dry fibrous structure basis, wherein the weight ratio of polymeric structurant to total level of surfactant and/or high melting point fatty material is 1 or less.

In one example, the filament-forming composition comprises from about 1% and/or from about 5% and/or from about 10% to about 50% and/or to about 40% and/or to about 30% and/or to about 20% by weight of the filament-forming composition of polymeric structurant; from about 1% and/or from about 5% and/or from about 10% to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of a volatile solvent, such as water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more fibrous elements and/or particles by any suitable spinning process, such as meltblowing, spunbonding, electro-spinning, and/or rotary spinning. In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt, such as a patterned belt to form a fibrous structure comprising the fibrous elements and/or particles.

Non-Limiting Examples for Making Fibrous Structures

The addition of particles may be accomplished during the formation of the embryonic fibers or after collection of the embryonic fibers on the patterned belts.

As shown in FIGS. 6 and 7, the fibrous elements of the present invention may be made as follows. Fibrous elements may be formed by means of a small-scale apparatus, a schematic representation of which is shown in FIGS. 6 and 7. A pressurized tank 62, suitable for batch operation is filled with a suitable filament-forming composition 48 for spinning. A pump 64, such as a Zenith®, type PEP II, having a capacity of 5.0 cubic centimeters per revolution (cc/rev), manufactured by Parker Hannifin Corporation, Zenith Pumps division, of Sanford, N.C., USA may be used to facilitate transport of the filament-forming composition to a spinning die 50. The flow of the filament-forming composition 48 from the pressurized tank 62 to the spinning die 50 may be controlled by adjusting the number of revolutions per minute (rpm) of the pump 64. Pipes 66 are used to connect the pressurized tank 62, the pump 64, and the spinning die 50.

The spinning die 50 shown in FIG. 7 has several rows of circular extrusion nozzles (fibrous element-forming holes 52) spaced from one another at a pitch P of about 1.524 millimeters (about 0.060 inches). The nozzles have individual inner diameters of about 0.305 millimeters (about 0.012 inches) and individual outside diameters of about 0.813 millimeters (about 0.032 inches). Each individual nozzle is encircled by an annular and divergently flared orifice (concentric attenuation fluid hole 56 to supply attenuation air to each individual melt capillary 54. The filament-forming composition 48 extruded through the nozzles is surrounded and attenuated by generally cylindrical, humidified air streams supplied through the orifices.

Attenuation air can be provided by heating compressed air from a source by an electrical-resistance heater, for example, a heater manufactured by Chromalox, Division of Emerson Electric, of Pittsburgh, Pa., USA. An appropriate quantity of steam was added to saturate or nearly saturate the heated air at the conditions in the electrically heated, thermostatically controlled delivery pipe. Condensate was removed in an electrically heated, thermostatically controlled, separator.

The embryonic fibrous elements are cooled by a quenching air stream having a temperature from about 5° C. (about 40° F.) to about 15° C. (about 50° F.) by a water chiller (not shown) supplied through cooling nozzles and discharged at an angle of about 90 degrees relative to the general orientation of the embryonic fibers being extruded. The cooled and solidified embryonic fibrous elements are collected on a collection device, such as, for example, a movable foraminous belt or patterned collection belt. The addition of a vacuum source directly under the formation zone may be used to aid collection of the fibers.

EXAMPLES

The following are non-limiting examples of the conditioner compositions described herein. It will be appreciated that other modifications of the present invention within the skill of those in the art can be undertaken without departing from the spirit and scope of this invention.

All parts, percentages, and ratios herein are by weight unless otherwise specified. Some components may come from suppliers as dilute solutions. The amount stated reflects the weight percent of the added material, unless otherwise specified.

Examples 1-29, in the tables below, were made as follows. In an appropriate container, the fatty amphiphile is heated to 90° C. with agitation. Under agitation, the components are added individually in the following order: (1) fatty amphiphile; (2) cationic surfactant; (3) polymeric structurant; (4) additional ingredients including the dispersing agent are added individually; and (5) acid. Each component is melted and fully incorporated before the next component is added.

Then, the final molten composition is allowed to deaerate to form the Molten Composition.

Visible Homogeneity of Molten Composition was determined by visual detection of the Molten Composition. The Molten Composition was determined homogeneous if particles and phase separation were not visually detectable. The Molten Composition was not homogeneous if there were visible particles and/or phase separation and/or cloudy. As used herein, "visual detection" means that a human viewer can visually discern the quality of the example with the unaided eye (excepting standard corrective lenses adapted to compensate for near-sightedness, farsightedness, or astigmatism, or other corrected vision) in lighting at least equal to the illumination of a standard 100-watt incandescent white light bulb at a distance of approximately 1 foot (0.30 m).

The Gel Network Formation was determined by heating the Molten Composition to 85° C. Water was also heated to 85° C. The water then was slowly added in a 10:1 ratio with mixing. If with visual detection, the cooled composition appeared creamlike and homogenous, then a gel network was present, which can help provide consumer acceptable conditioning. If the composition appeared to have multiple phases and/or had an appearance resembling oil and water, then there was no gel network and this example may not provide consumer acceptable conditioning.

TABLE 1

Inventive Conditioner Examples 1-6

| | Ex. 1 | Ex. 2 | Ex. 3 | Ex. 4 | Ex. 5 | Ex. 6 |
|---|---|---|---|---|---|---|
| Distilled Water | 2.0 | 2.0 | 2.0 | 1.8 | 2.0 | 2.0 |
| Stearamidopropyl Dimethylamine[1] | 19.6 | 19.6 | 19.6 | 19.6 | 23 | 23.9 |
| Stearyl Alcohol | 44.2 | 42.2 | 42.9 | 44.8 | 40.5 | 45.2 |
| 1-Hexadecanol | 22.1 | 21.1 | 21.4 | 22.3 | 16.7 | 22.6 |
| Lauroyl Methyl Glucamide[3] | 0.0 | 2.9 | 2.9 | 2.9 | 8.3 | 0.0 |
| Polyvinyl pyrrolidone[4] | 3.9 | 3.9 | 3.9 | 3.9 | 3.9 | 3.9 |
| Salicylic acid[5] | 8.2 | 8.2 | 7.3 | 0.0 | 0.0 | 0.0 |
| Lactic acid[6] | 0.0 | 0.0 | 0.0 | 4.7 | 5.6 | 0.0 |
| 2,4 Dihydroxybenzoic acid[11] | 0.0 | 0.0 | 0.0 | 0.0 | 0.0 | 2.4 |
| Visible Homogeneity of Molten Composition | Yes | Yes | Yes | Yes | Yes | Yes |
| Gel Network Formation | Yes | Yes | Yes | Yes | Yes | Yes |

TABLE 2

Inventive Conditioner Examples 7-12

| | Ex. 7 | Ex. 8 | Ex. 9 | Ex. 10 | Ex. 11 | Ex. 12 |
|---|---|---|---|---|---|---|
| Distilled Water | 2.0 | 2.0 | 2.0 | 2.0 | 2.0 | 2.0 |
| Stearamidopropyl Dimethylamine[1] | 19.6 | 19.6 | 0.0 | 0.0 | 0.0 | 0.0 |
| Behenamidopropyl Dimethylamine[2] | 0.0 | 0.0 | 19.6 | 19.6 | 19.6 | 19.6 |
| Stearyl Alcohol | 44.21 | 40.6 | 44.2 | 42.2 | 42.9 | 44.8 |
| 1-Hexadecanol | 22.09 | 20.3 | 22.1 | 21.1 | 21.4 | 22.3 |
| Lauroyl Methyl Glucamide[3] | 0.0 | 8.8 | 0.0 | 2.9 | 2.9 | 2.9 |
| Polyvinyl pyrrolidone[4] | 3.9 | 3.9 | 3.9 | 3.9 | 3.9 | 3.9 |
| Salicylic acid[5] | 0.0 | 0.0 | 8.2 | 8.2 | 7.3 | 0.0 |
| Lactic acid[6] | 0.0 | 0.0 | 0.0 | 0.0 | 0.0 | 4.7 |
| 2,4 Dihydroxybenzoic acid[11] | 8.2 | 0.0 | 0.0 | 0.0 | 0.0 | 0.0 |
| Sorbic Acid[12] | 0.0 | 4.7 | 0.0 | 0.0 | 0.0 | 0.0 |
| Visible Homogeneity of Molten Composition | Yes | Yes | Yes | Yes | Yes | Yes |
| Gel Network Formation | Yes | Yes | Yes | Yes | Yes | Yes |

TABLE 3

Inventive Conditioner Examples 13-18

| | Ex. 13 | Ex. 14 | Ex. 15 | Ex. 16 | Ex. 17 | Ex. 18 |
|---|---|---|---|---|---|---|
| Distilled Water | 2.0 | 2.0 | 2.0 | 2.0 | 2.0 | 2.0 |
| Stearamidopropyl Dimethylamine[1] | 19.6 | 19.6 | 19.6 | 19.6 | 19.6 | 0.0 |
| Behentrimonium Methosulfate[2] | 0.0 | 0.0 | 0.0 | 0.0 | 0.0 | 24.5 |
| Stearyl Alcohol | 49.43 | 50.56 | 50.30 | 50.60 | 50.64 | 43.03 |
| 1-Hexadecanol | 20.26 | 20.72 | 20.61 | 20.74 | 20.75 | 17.63 |
| Lauroyl Methyl Glucamide[3] | 0.0 | 0.0 | 0.0 | 0.0 | 0.0 | 8.82 |
| Polyvinyl pyrrolidone[4] | 3.9 | 3.9 | 3.9 | 3.9 | 3.9 | 3.92 |
| Lactic acid[6] | 4.79 | 0.0 | 0.0 | 0.0 | 0.0 | 0.1 |
| Acetic Acid[7] | 0.0 | 3.20 | 0.0 | 0.0 | 0.0 | 0.0 |
| Malic Acid[8] | 0.0 | 0.0 | 3.57 | 0.0 | 0.0 | 0.0 |
| Succinic Acid[9] | 0.0 | 0.0 | 0.0 | 3.14 | 0.0 | 0.0 |
| Maleic Acid[10] | 0.0 | 0.0 | 0.0 | 0.0 | 3.09 | 0.0 |
| Visible Homogeneity of Molten Composition | Yes | Yes | Yes | Yes | Yes | Yes |
| Gel Network Formation | Yes | Yes | Yes | Yes | Yes | Yes |

Suppliers for raw materials for the Examples in Table 1, Table 2, and Table 3.
1. Stearamidopropyl Dimethylamine from Croda™
2. Behentrimonium Methosulfate from Clariant™
3. Glucotain Clean RM from Clariant™
4. PVP K120 from Ashland™
5. Salicylic acid from Sigma Aldrich® S5922-100G
6. Lactic Acid from Sigma Aldrich® W261106-1KG-K
7. Acetic Acid from Sigma Aldrich® 151777-50g
8. Malic Acid from Sigma Aldrich® M8304-10G
9. Succinic Acid from Sigma Aldrich® 797987-100G
10. Maleic Acid from Sigma Aldrich® M0375-100G
11. 2,4 Dihydroxybenzoic acid 11 from Sigma Aldrich® D109401-100G
12. Sorbic Acid from Sigma Aldrich® S1626-100G The inventive examples in Examples 1-17 contain salicylic acid, lactic acid, acetic acid, malic acid, succinic acid, sorbic acid, 2,4-dihydroxybenzoic acid, or maleic acid. These acids are soluble in the Molten Composition and the examples have homogenous Molten Compositions. Since the Molten Composition is homogenous, it is likely that if the Molten Composition is spun into fibrous elements. Also, Examples 1-17 all formed a gel network. If the Molten Composition was formed into a fibrous structure, it is believed that the fibrous structure would have a latent gel network that when water is added during use will form a gel network and the fibrous structure will provide a consumer acceptable conditioning.

TABLE 4

Comparative Conditioner Examples 19-24

| | Ex. 19 | Ex. 20 | Ex. 21 | Ex. 22 | Ex. 23 | Ex. 24 |
|---|---|---|---|---|---|---|
| Distilled Water | 2.0 | 2.0 | 2.0 | 2.0 | 2.0 | 2.0 |
| Stearamido-propyl Dimethyl-amine[1] | 19.6 | 19.6 | 19.6 | 19.6 | 19.6 | 19.6 |
| Palmitic Acid | 13.72 | 13.72 | 27.44 | 49.0 | 0.0 | 0.0 |
| Stearyl Alcohol | 40.5 | 38.5 | 29.4 | 15.0 | 46.4 | 38.7 |
| 1-Hexadecanol | 20.3 | 19.3 | 14.7 | 7.5 | 23.2 | 17.9 |
| Lauroyl Methyl Glucamide[2] | 0.0 | 2.9 | 2.9 | 2.9 | 2.9 | 2.9 |
| Polyvinyl pyrrolidone[3] | 3.9 | 3.9 | 3.9 | 3.9 | 3.9 | 3.9 |
| Hydrochloric Acid | 0.0 | 0.0 | 0.0 | 0.0 | 2.0 | 0.0 |
| Oleic Acid[5] | 0.0 | 0.0 | 0.0 | 0.0 | 0.0 | 15.0 |
| Visible Homogeneity of Molten Composition | Yes | Yes | Yes | Yes | No | No |
| Gel Network Formation | No | No | No | No | N/A | N/A |

TABLE 5

Comparative Conditioner Examples 25-30

| | Ex. 25 | Ex. 26 | Ex. 27 | Ex. 28 | Ex. 29 | Ex. 20 |
|---|---|---|---|---|---|---|
| Distilled Water | 2.0 | 2.0 | 2.0 | 2.0 | 2.0 | 2.0 |
| Stearamido-propyl Dimethyl-amine[1] | 19.6 | 19.6 | 19.6 | 19.6 | 19.6 | 19.6 |
| Stearyl Alcohol | 44.6 | 47.3 | 48.4 | 47.2 | 45.9 | 52.8 |
| 1-Hexadecanol | 22.3 | 19.4 | 19.9 | 19.3 | 18.8 | 21.7 |
| Lauroyl Methyl Glucamide[2] | 2.9 | 0.0 | 0.0 | 0.0 | 0.0 | 0.0 |
| Polyvinyl pyrrolidone[3] | 3.9 | 3.9 | 3.9 | 3.9 | 3.9 | 3.9 |
| Citric Acid | 4.7 | 0.0 | 0.0 | 0.0 | 0.0 | 0.0 |
| L glutamic acid[6] | 0.0 | 7.8 | 0.0 | 0.0 | 0.0 | 0.0 |
| fumaric acid[7] | 0.0 | 0.0 | 6.1 | 0.0 | 0.0 | 0.0 |
| tartaric acid[8] | 0.0 | 0.0 | 0.0 | 8.0 | 0.0 | 0.0 |
| L glutamic hydrochloride[9] | 0.0 | 0.0 | 0.0 | 0.0 | 9.8 | 0.0 |
| Visible Homogeneity of Molten Composition | No | No | No | No | No | Yes |
| Gel Network Formation | N/A | N/A | N/A | N/A | N/A | No |

Suppliers for raw materials for the Examples in The inventive examples in Examples 1-17 contain salicylic acid, lactic acid, acetic acid, malic acid, succinic acid, sorbic acid, 2,4-dihydroxybenzoic acid, or maleic acid. These acids are soluble in the Molten Composition and the examples have homogenous Molten Compositions. Since the Molten Composition is homogenous, it is likely that the Molten Composition is spun into fibrous elements. Also, Examples 1-17 all formed a gel network. If the Molten Composition was formed into a fibrous structure, it is believed that the fibrous structure would have a latent gel network that when water is added during use will form a gel network and the fibrous structure will provide a consumer acceptable conditioning.
Table 4 and Table 5.
 1. Stearamidopropyl Dimethylamine from Croda™
 2. Glucotain Clean RM from Clariant™
 3. PVP K120 from Ashland™
 4. Amodimethicone from Momentive™ Performance Materials
 5. Oleic acid from Sigma Aldrich® 01008-25G
 6. L glutamic acid from Sigma Aldrich® W328502-1KG-K
 7. Fumaric acid from Sigma Aldrich® 47910-100g
 8. Tartaric acid from Sigma Aldrich® T109-500G-A
 9. L glutamic hydrochloride from Sigma Aldrich® G2128-100G The comparative examples in Examples 19-30 contain citric acid, L-glutamic acid, fumaric acid, tartaric acid, L-glutamic hydrochloride, hydrochloric acid, and oleic acid. These acids are not soluble in the Molten Composition. In Examples 23-29 the acid did not dissolve in the Molten Composition and formed precipitate. Therefore, the second step, cooling the composition to ambient temperature to determine whether there was a gel network could not be performed. In Examples 19-22 and 30 the Molten Composition is homogenous; however, it did not form a gel network when the Molten Composition was cooled to ambient temperature. If this composition could be made into fibrous structures, a gel network would not form when the structure is hydrated and therefore these compositions would likely not provide consumer acceptable conditioning. In certain examples, it can be advantageous for the fibrous elements to be free of or substantially free of citric acid, L-glutamic acid, fumaric acid, tartaric acid, L-glutamic hydrochloride, hydrochloric acid, and oleic acid.

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. The samples tested are "usable units." "Usable units" as used herein means sheets, flats from roll stock, pre-converted flats, and/or single or multi-ply products. All tests are conducted under the same environmental conditions and in such conditioned room. Do not test samples that have defects such as wrinkles, tears, holes, and like. Samples conditioned as described herein are considered dry samples (such as "dry filaments") for testing purposes. All instruments are calibrated according to manufacturer's specifications.

Basis Weight Test Method

Basis weight of a fibrous structure is measured on stacks of twelve usable units using a top loading analytical balance with a resolution of ±0.001 g. The balance is protected from air drafts and other disturbances using a draft shield. A precision cutting die, measuring 3.500 in ±0.0035 in by 3.500 in ±0.0035 in is used to prepare all samples.

With a precision cutting die, cut the samples into squares. Combine the cut squares to form a stack twelve samples thick. Measure the mass of the sample stack and record the result to the nearest 0.001 g.

The Basis Weight is calculated in lbs/3000 ft² or g/m² as follows:

Basis Weight=(Mass of stack)/[(Area of 1square in stack)×(No. of squares in stack)]

For example,

Basis Weight(lbs/3000 ft²)=[[Mass of stack(g)/453.6 (g/lbs)]/[12.25(in²)/144(in²/ft²)×12]]×3000 or,

Basis Weight(g/m²)=Mass of stack(g)/[79.032(cm²)/ 10,000(cm²/m²)×12]

Report result to the nearest 0.1 lbs/3000 ft² or 0.1 g/m². Sample dimensions can be changed or varied using a similar precision cutter as mentioned above, so as at least 100 square inches of sample area in stack.

Water Content Test Method

The water (moisture) content present in a fibrous element and/or particle and/or fibrous structure is measured using the following Water Content Test Method. A fibrous element and/or particle and/or fibrous structure or portion thereof ("sample") in the form of a pre-cut sheet is placed in a conditioned room at a temperature of 23° C.±1.0° C. and a relative humidity of 50%±2% for at least 24 hours prior to testing. Each fibrous structure sample has an area of at least 4 square inches, but small enough in size to fit appropriately on the balance weighing plate. Under the temperature and humidity conditions mentioned above, using a balance with at least four decimal places, the weight of the sample is recorded every five minutes until a change of less than 0.5% of previous weight is detected during a 10 minute period. The final weight is recorded as the "equilibrium weight". Within 10 minutes, the samples are placed into the forced air oven on top of foil for 24 hours at 70° C.±2° C. at a relative humidity of 4%±2% for drying. After the 24 hours of drying, the sample is removed and weighed within 15 seconds. This weight is designated as the "dry weight" of the sample.

The water (moisture) content of the sample is calculated as follows:

% Water in sample=100%×(Equilibrium weight of sample−Dry weight of sample)/Dry weight of sample The % Water (moisture) in sample for 3 replicates is averaged to give the reported % Water (moisture) in sample. Report results to the nearest 0.1%.

Thickness Method

Thickness of a fibrous structure is measured by cutting 5 samples of a fibrous structure sample such that each cut sample is larger in size than a load foot loading surface of a VIR Electronic Thickness Tester Model II available from Thwing-Albert Instrument Company, Philadelphia, Pa. Typically, the load foot loading surface has a circular surface area of about 3.14 in². The sample is confined between a horizontal flat surface and the load foot loading surface. The load foot loading surface applies a confining pressure to the sample of 15.5 g/cm². The thickness of each sample is the resulting gap between the flat surface and the load foot loading surface. The thickness is calculated as the average thickness of the five samples. The result is reported in millimeters (mm).

Shear Viscosity Test Method

The shear viscosity of a filament-forming composition of the present invention is measured using a capillary rheometer, Goettfert Rheograph 6000, manufactured by Goettfert USA of Rock Hill S.C., USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A preheated to die test temperature, 60 g sample of the filament-forming composition is loaded into the barrel section of the rheometer. Rid the sample of any entrapped air. Push the sample from the barrel through the capillary die at a set of chosen rates 1,000-10, 000 seconds⁻¹. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta=K\gamma^{n-1}$, wherein K is the material's viscosity constant, n is the material's thinning index and γ is the shear rate. The reported apparent shear viscosity of the filament-forming composition herein is calculated from an interpolation to a shear rate of 3,000 sec-1 using the power law relation.

Diameter Test Method

The diameter of a discrete fibrous element or a fibrous element within a fibrous structure is determined by using a Scanning Electron Microscope (SEM) or an Optical Microscope and an image analysis software. A magnification of 200 to 10,000 times is chosen such that the fibrous elements are suitably enlarged for measurement. When using the SEM, the samples are sputtered with gold or a palladium compound to avoid electric charging and vibrations of the fibrous element in the electron beam. A manual procedure for determining the fibrous element diameters is used from the image (on monitor screen) taken with the SEM or the optical microscope. Using a mouse and a cursor tool, the edge of a randomly selected fibrous element is sought and then measured across its width (i.e., perpendicular to fibrous element direction at that point) to the other edge of the fibrous element. A scaled and calibrated image analysis tool provides the scaling to get actual reading in μm. For fibrous elements within a fibrous structure, several fibrous element are randomly selected across the sample of the fibrous structure using the SEM or the optical microscope. At least two portions of the fibrous structure are cut and tested in this manner. Altogether at least 100 such measurements are made and then all data are recorded for statistical analysis. The recorded data are used to calculate average (mean) of the fibrous element diameters, standard deviation of the fibrous element diameters, and median of the fibrous element diameters.

Another useful statistic is the calculation of the amount of the population of fibrous elements that is below a certain upper limit. To determine this statistic, the software is programmed to count how many results of the fibrous element diameters are below an upper limit and that count (divided by total number of data and multiplied by 100%) is reported in percent as percent below the upper limit, such as percent below 1 micrometer diameter or %-submicron, for example. We denote the measured diameter (in μm) of an individual circular fibrous element as di.

In the case that the fibrous elements have non-circular cross-sections, the measurement of the fibrous element diameter is determined as and set equal to the hydraulic diameter which is four times the cross-sectional area of the fibrous element divided by the perimeter of the cross-section of the fibrous element (outer perimeter in case of hollow fibrous elements). The number-average diameter, alternatively average diameter is calculated as:

$$d_{num} = \frac{\sum_{i=1}^{n} d_i}{n}$$

Fibrous Element Composition Test Method

In order to prepare fibrous elements for fibrous element composition measurement, the fibrous elements must be conditioned by removing any coating compositions and/or materials present on the external surfaces of the fibrous elements that are removable. An example of a method for doing so is washing the fibrous elements 3 times with a suitable solvent that will remove the external coating while leaving the fibrous elements unaltered. The fibrous elements are then air dried at 23° C.±1.0° C. until the fibrous elements comprise less than 10% moisture. A chemical analysis of the conditioned fibrous elements is then completed to determine the compositional make-up of the fibrous elements with respect to the filament-forming materials and the active agents and the level of the filament-forming materials and active agents present in the fibrous elements.

The compositional make-up of the fibrous elements with respect to the filament-forming material and the active agents can also be determined by completing a cross-section analysis using TOF-SIMs or SEM. Still another method for determining compositional make-up of the fibrous elements uses a fluorescent dye as a marker. In addition, as always, a manufacturer of fibrous elements should know the compositions of their fibrous elements.

Lamellar Structure Test Method

The Lamellar Structure Test Method makes use of small-angle x-ray scattering (SAXS) to determine if a lamellar structure is present in a dissolvable solid structure either in a conditioned, dry state or upon wetting after having been previously in a conditioned, dry state. Dissolvable solid structure are conditioned at a temperature of 23° C.±2.0° C. and a relative humidity of 40%±10% for a minimum of 12 hours prior to the test. Dissolvable solid structure conditioned as described herein are considered to be in a conditioned, dry state for the purposes of this invention. All instruments are calibrated according to manufacturer's specifications.

Dry Sample Preparation

To prepare a sample to be analyzed directly in the conditioned, dry state, a specimen of about 1.0 cm diameter disc is isolated from the center of an dissolvable solid structure and is loaded into a conventional SAXS solid sample holder with aperture diameter between 4 and 5 mm. (Multiple specimen discs may be extracted from multiple dissolvable solid structures and stacked, if necessary, to ensure sufficient scattering cross-section.) The loaded sample holder is immediately placed in the appropriate instrument for data collection.

Wet Sample Preparation

Three samples are analyzed upon wetting from the dry, conditioned state. Specimens are extracted from dry, conditioned dissolvable solid structure and hydrated with water in order to achieve three separate preparations each possessing a different material-to-water mass ratio. The three different material-to-water mass ratios to be prepared are 1:5; 1:9; and 1:20. For each mass ratio, one or more specimens (as needed) 1 cm in diameter are extracted from the geometric centers of one or more dissolvable solid structure in the dry, conditioned state are hydrated with 23° C.±2.0° C. filtered deionized (DI) water in order to achieve the intended material-to-water mass ratio. Each of the three material/water mixtures (each corresponding to a different mass ratio) is stirred under low shear gently by hand at room temperature using a spatula until visibly homogenous. Each material/water mixture is then immediately loaded into a separate quartz capillary tube with outer diameter 2.0 mm in diameter and 0.01 mm wall thickness. The capillary tubes are immediately sealed with a sealant such as an epoxy resin to prevent the evaporation of water from the preparations. The sealant is permitted to dry for at least 2 hours and until dry at a temperature of 23° C.±2.0° C. prior to sample analysis. Each prepared wet sample is introduced into an appropriate SAXS instrument and data are collected.

Testing and Analysis

Samples are tested using SAXS in 2-dimension (2D) transmission mode over an angular range in of 0.3° to 3.0° 2θ, to observe the presence and spacing of any intensity bands in the x-ray scatter pattern. The test is conducted using a SAXS instrument (such as the NanoSTAR, Bruker AXS Inc., Madison, Wis., U.S.A., or equivalent). Conditioned, dry samples are analyzed under ambient pressure. Sealed liquid samples are analyzed in the instrument under vacuum. All samples are analyzed at a temperature of 23° C.±2.0° C. The x-ray tube of the instrument is operated sufficient power to ensure that any scattering bands present are clearly detected. The beam diameter is 550±50 m. One suitable set of operating conditions includes the following selections: NanoSTAR instrument; micro-focus Cu x-ray tube; 45 kV and 0.650 mA power; Vantec2K 2-Dimensional area detector; collection time of 1200 seconds; and distance between the sample and detector of 112.050 cm. The raw 2-D SAXS scattering pattern is integrated azimuthally to determine intensity (1) as a function of the scattering vector (q), which are expressed throughout this method units of reciprocal angstroms ($Å^{-1}$). The values for q are calculated by the SAXS instrument according to the following equation:

$$q = \frac{4\pi}{\lambda} \sin\theta$$

where:

2θ is the scattering angle; and

λ is the wavelength used.

For each integrated SAXS analyzed, the value of q in $Å^{-1}$ corresponding to each intensity peak on the plot of I vs q is identified and recorded from smallest to largest. (One of skill in the art knows that a sharp peak in q near the origin corresponds to scatter off of the beam stop and is disregarded in this method.) The value of q corresponding to the first intensity peak (the lowest value of q) is referred to as q*.

For a sample analyzed directly in the dry, conditioned state, if an intensity peak is present at 2 q*±0.002 $Å^{-1}$, the sample is determined to exhibit a lamellar structure, and the characteristic d-spacing parameter is defined as 2π/q*. If no intensity peak if present at 2 q*±0.002 $Å^{-1}$, the sample analyzed directly in the dry, conditioned state is determined to not exhibit a lamellar structure.

For a sample analyzed upon wetting from the dry, conditioned state, if an intensity peak is present at 2 q*±0.002 $Å^{-1}$, the sample is determined to exhibit a lamellar structure, and the characteristic d-spacing parameter is defined as 2/q*. If no intensity peak is present at 2 q*±0.002 $Å^{-1}$, the sample is determined to not exhibit a lamellar structure. If a lamellar structure is determined to be present in at least any one of the three material/water ratios prepared, then this material is determined to exhibit a lamellar structure upon wetting. If no intensity peak is present at 2 q*±0.002 Å⁻¹, in any of the three material/water ratios prepared, the material is determined to not exhibit a lamellar structure upon wetting.

Hand Dissolution Method

Materials Needed:

Fibrous structures to be tested: 3-5 fibrous structures (finished product samples) are tested so that an average of the number of strokes for each if the individual fibrous structure samples is calculated and recorded as the Average Hand Dissolution value for the fibrous structure. For this method, the entire consumer saleable or consumer use fibrous structure is tested. If the entire consumer saleable or consumer use fibrous structure has a footprint greater than 50 cm², then first cut the fibrous structure to have a footprint of 50 cm².

Nitrile Gloves 10 cc syringe

Plastic Weigh boat (~3 in×3 in)

100 mL Glass beaker

Water (City of Cincinnati Water or equivalent having the following properties: Total Hardness=155 mg/L as $CaCO_2$; Calcium content=33.2 mg/L; Magnesium content=17.5 mg/L; Phosphate content=0.0462 mg/L). Water used is water 7 grains per gallon (gpg) hardness and 40° C.+/−5° C.

Protocol:

Add 80 mL of water to glass beaker.

Heat water in beaker until water is at a temperature of 40° C.+/−5° C.

Transfer 15 mL of the water from the beaker into the weigh boat via the syringe.

Within 10 seconds of transferring the water to the weigh boat, place fibrous structure sample in palm of gloved hand (hand in cupped position in non-dominant hand to hold fibrous structure sample).

Using dominant hand, add water quickly from the weigh boat to the fibrous structure sample and allow to immediately wet for a period of 5-10 seconds.

Rub with opposite dominant hand (also gloved) in 2 rapid circular strokes.

Visually examine the fibrous structure sample in hand after the 2 strokes. If fibrous structure sample is completely dissolved, record number of strokes=2 Dissolution Strokes. If not completely dissolved, rub remaining fibrous structure sample for 2 more circular strokes (4 total) and observe degree of dissolution. If the fibrous structure sample contains no solid pieces after the 2 additional strokes, record number of strokes=4 Dissolution Strokes. If after the 4 strokes total, the fibrous structure sample still contains solid pieces of un-dissolved fibrous structure sample, continue rubbing remaining fibrous structure sample in additional 2 circular strokes and check if there are any remaining solid pieces of fibrous structure sample after each additional 2 strokes until fibrous structure sample is completely dissolved or until reaching a total of 30 strokes, whichever comes first. Record the total number of strokes. Record 30 Dissolution Strokes even if solid fibrous structure sample pieces remain after the maximum of 30 strokes.

Repeat this process for each of the additional 4 fibrous structure samples.

Calculate the arithmetic mean of the recorded values of Dissolution Strokes for the 5 individual fibrous structure samples and record as the Average Hand Dissolution Value for the fibrous structure. The Average Hand Dissolution Value is reported to the nearest single Dissolution Stroke unit.

Combinations

A. A fibrous structure comprising a plurality of fibrous elements comprising:
  a. from about 1 wt % to about 50 wt % of a polymeric structurant, alternatively from about 1 wt. % to about 30 wt. % polymeric structurant, alternatively from about 1 wt. % to about 10 wt. % polymeric structurant, alternatively from about 2 wt. % to about 6 wt. % polymeric structurant, and alternatively from about 3 wt. % to about 5 wt. % polymeric structurant; wherein the polymeric structurant comprises a weight average molecular weight of from about 10,000 to about 6,000,000 g/mol, alternatively from about 3,000,000 g/mol to about 5,000,000 g/mol, and alternatively from about 3,000,000 g/mol to about 5,000,000 g/mol;
  b. from about 10 wt % to about 85 wt % of a fatty material, alternatively from about 20 wt. % to about 70 wt. % of a fatty material, alternatively from about 50 wt. % to about 70 wt. % of a fatty material, alternatively from about 10 wt. % to about 20 wt. % of a fatty material, wherein the fatty material comprises a carbon chain length C12-C22 or mixtures thereof and wherein the melting point is above 25° C., alternatively 40° C. or higher, alternatively 45° C. or higher, alternatively 50° C. or higher;
  c. from about 1 wt % to about 60 wt % of a cationic surfactant, alternatively from about 10 wt. % to about 50 wt. % cationic surfactant, alternatively from about 20 wt. % to about 40 wt. % cationic surfactant, wherein the cationic surfactant is selected from the group consisting of a mono-long alkyl amine, a tertiary amine, and combinations thereof;
  d. from about 0.1 wt. % to about 10 wt. % of an oil soluble acid, alternatively from about 0.1 wt. % to about 9 wt. % of an oil soluble acid, alternatively about 0.25 wt. % to about 7 wt. %. of an oil soluble acid, alternatively from about 0.3 wt. % to about 5 wt. % of an oil soluble acid; wherein the oil soluble acid is selected from the group consisting of salicylic acid, lactic acid, acetic acid, malic acid, succinic acid, sorbic acid, 2,4-dihydroxybenzoic acid, maleic acid, and combinations thereof; wherein the oil soluble acid is dispersed throughout the fibrous elements.

B. The fibrous structure of paragraph A, wherein the cationic surfactant comprises a mono-long alkyl amine.

C. The fibrous element of paragraph B, wherein the mono-long alkyl amine comprises one long alkyl chain of from 12 to 30 carbon atoms, alternatively from 16 to 24 carbon atoms, alternatively from 18 to 22 carbon atoms.

D. The fibrous element of paragraph B, wherein the mono-long alkyl amine is selected from the group consisting of stearamidopropyl dimethylamine, behenamidopropyl dimethylamine, and combinations thereof.

E. The fibrous structure of paragraphs A-D, wherein a lamellar structure is formed upon addition of water to the dissolvable solid structure in the ratio of about 10:1.

F. The fibrous structure of paragraphs A-E, wherein the fibrous elements are homogenous.

G. The fibrous structure of paragraphs A-F, further comprising from about 1 wt % to about 30 wt % of a dispersing agent, alternatively from about 5 wt. % to about 15 wt. % dispersing agent, and alternatively from about 5 wt. % to about 10 wt % dispersing agent wherein the dispersing agent is selected from the group consisting of a surfactant from the nonionic class of alkyl glucamides, reverse alkyl glucamides, cocoamiodpropyl betaines, alkyl glucoside, triethanol amine, cocamide MEAs, and mixtures thereof.

H. The fibrous structure of paragraphs A-D, wherein the fatty material comprises one or more fatty alcohols selected from the group consisting of: cetyl alcohol, stearyl alcohol, behenyl alcohol, and mixtures thereof.
I. The fibrous structure of paragraphs A-H, wherein the fatty material comprises cetyl alcohol and stearyl alcohol at a ratio from about 1:9 to 9:1, alternatively from about 1:4 to about 4:1, alternatively from about 1:2.3 to about 1.5:1.
J. The fibrous structure of paragraphs A-I, wherein the polymeric structurant is selected from the group consisting of: pullulan, hydroxypropylmethyl cellulose, hydroxyethyl cellulose, hydroxypropyl cellulose, polyvinyl pyrrolidone, carboxymethyl cellulose, sodium alginate, xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, carboxylated polyvinyl alcohol, sulfonated polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, and mixtures thereof.
K. The fibrous structure of paragraph J, wherein the polymeric structurant comprises polyvinyl pyrrolidone.
L. The fibrous structure of paragraphs A-K, wherein the structure is substantially free of citric acid, L-glutamic acid, fumaric acid, tartaric acid, L-glutamic hydrochloride, hydrochloric acid, and oleic acid.
M. The fibrous structure of paragraphs A-L, further comprising an extensional aid having a weight-average molecular weight of from about 500,000 Da to about 25,000,000 Da, alternatively from about 800,000 Da to about 22,000,000 Da, alternatively from about 1,000,000 Da to about 20,000,000 Da, and alternatively from about 2,000,000 Da to about Da 15,000,000.
N. The fibrous structure of paragraphs A-M, further comprising an extensional aid selected from the group consisting of alginates, carrageenans, pectin, chitin, guar gum, xanthum gum, agar, gum arabic, karaya gum, tragacanth gum, locust bean gum, alkylcellulose, modified and unmodified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.
O. A method for conditioning hair comprising:
a. wetting the structure of paragraphs A-N with water to dissolve the structure;
b. applying the dissolved structure to the hair to condition it;
c. rinsing the dissolved structure from the hair.
P. The method of paragraph O wherein the hair comprises fine hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited.

The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fibrous structure comprising a plurality of fibrous elements comprising:
    a. from about 1 wt % to about 50 wt % of a polymeric structurant having a weight average molecular weight of from about 10,000 to about 6,000,000 g/mol;
    b. from about 10 wt % to about 85 wt % of a fatty material having a carbon chain length C12-C22 or mixtures thereof, wherein the melting point is above 25° C.;
    c. from about 1 wt % to about 60 wt % of a cationic surfactant selected from a mono-long alkyl amine, a tertiary amine, and combinations thereof;
    d. from about 0.1 wt. % to about 10 wt. % of an oil soluble acid selected from the group consisting of salicylic acid, lactic acid, acetic acid, malic acid, succinic acid, sorbic acid, 2,4-dihydroxybenzoic acid, maleic acid, and combinations thereof;
    wherein the oil soluble acid is dispersed throughout the fibrous elements;
    wherein the plurality of fibrous elements are inter-entangled or otherwise associated with one another to form the fibrous structure.

2. The fibrous structure of claim 1, wherein the cationic surfactant comprises a mono-long alkyl amine.

3. The fibrous element of claim 2, wherein the mono-long alkyl amine is selected from the group consisting of stearamidopropyl dimethylamine, behenamidopropyl dimethylamine, and combinations thereof.

4. The fibrous structure of claim 1, wherein a lamellar structure is formed upon addition of water to the dissolvable solid structure in the ratio of about 10:1.

5. The fibrous structure of claim 1, wherein the fibrous elements are homogenous.

6. The fibrous structure of claim 1, further comprising from about 1 wt % to about 30 wt % of a dispersing agent is selected from the group consisting of a surfactant from the nonionic class of alkyl glucamides, reverse alkyl glucamides, cocoamiodpropyl betaines, alkyl glucoside, triethanol amine, cocamide MEAs, and mixtures thereof.

7. The fibrous structure of claim 1, comprising from about 10 wt % to about 50 wt % of cationic surfactant.

8. The fibrous structure of claim 7, comprising from about 20 wt % to about 40 wt % of cationic surfactant.

9. The fibrous structure of claim 1, comprising from about 1 wt % to about 30 wt % of polymeric structurant.

10. The fibrous structure of claim 9, comprising from about 1 wt % to about 10 wt % polymeric structurant.

11. The fibrous structure of claim 10, comprising from about 2 wt % to about 6 wt % of a polymeric structurant.

12. The fibrous structure of claim 1, wherein the fatty material comprises one or more fatty alcohols selected from the group consisting of cetyl alcohol, stearyl alcohol, behenyl alcohol, and mixtures thereof.

13. The fibrous structure of claim 1, wherein the polymeric structurant is selected from the group consisting of: pullulan, hydroxypropylmethyl cellulose, hydroxyethyl cellulose, hydroxypropyl cellulose, polyvinyl pyrrolidone, carboxymethyl cellulose, sodium alginate, xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, carboxylated polyvinyl alcohol, sulfonated polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, and mixtures thereof.

14. The fibrous structure of claim 13, wherein the polymeric structurant comprises polyvinyl pyrrolidone.

15. The fibrous structure of claim 1, wherein the structure is substantially free of citric acid, L-glutamic acid, fumaric acid, tartaric acid, L-glutamic hydrochloride, hydrochloric acid, and oleic acid.

16. A method for conditioning hair comprising:
   a. wetting the structure of claim 1 with water to dissolve the structure;
   b. applying the dissolved structure to the hair to condition it;
   c. rinsing the dissolved structure from the hair.

17. The fibrous structure of claim 1, wherein at least 50% of the fibrous elements comprise an average diameter less than about 150 microns.

* * * * *